(12) United States Patent
Solar et al.

(10) Patent No.: US 7,559,935 B2
(45) Date of Patent: Jul. 14, 2009

(54) TARGET DEPTH LOCATORS FOR TRAJECTORY GUIDE FOR INTRODUCING AN INSTRUMENT

(75) Inventors: Matthew S. Solar, Indialantic, FL (US); Thomas L. Bridges, Melbourne Beach, FL (US); Thomas I. Miller, Palm Bay, FL (US); James G. Skakoon, St. Paul, MN (US); David Lee, Melbourne, FL (US)

(73) Assignee: Medtronic, Inc., Minneapolis, MN (US)

( * ) Notice: Subject to any disclaimer, the term of this patent is extended or adjusted under 35 U.S.C. 154(b) by 1040 days.

(21) Appl. No.: 10/370,083

(22) Filed: Feb. 20, 2003

(65) Prior Publication Data

US 2004/0167542 A1 Aug. 26, 2004

(51) Int. Cl.
*A61B 19/00* (2006.01)

(52) U.S. Cl. ...................................... 606/130
(58) Field of Classification Search ................. 606/130, 606/129; 600/401–407
See application file for complete search history.

(56) References Cited

U.S. PATENT DOCUMENTS

| | | | |
|---|---|---|---|
| 1,129,333 A | 2/1915 | Clarke | |
| 1,664,210 A | 3/1928 | Hall | |
| 2,119,649 A | 6/1938 | Roosen | |
| 2,135,160 A | 11/1938 | Beekhuis | |
| 2,686,890 A | 8/1954 | Davis | |
| 3,016,899 A | 1/1962 | Stenvall | |
| 3,017,887 A | 1/1962 | Heyer | 128/348 |
| 3,055,370 A | 9/1962 | McKinney et al. | 128/303 |
| 3,055,371 A | 9/1962 | Kulick et al. | |
| 3,115,140 A | 12/1963 | Volkman | |
| 3,135,263 A | 6/1964 | Connelley, Jr. | 128/303 |
| 3,223,087 A | 12/1965 | Vladyka et al. | 128/303.13 |
| 3,262,452 A | 7/1966 | Hardy et al. | |
| 3,273,559 A | 9/1966 | Evans | |
| 3,282,152 A | 11/1966 | Myer | |
| 3,402,710 A | 9/1968 | Paleschuck | |
| 3,444,861 A | 5/1969 | Schulte | |
| 3,457,922 A | 7/1969 | Ray | 128/303 |
| 3,460,537 A | 8/1969 | Zeis | |
| 3,508,552 A | 4/1970 | Hainault | 128/303 |

(Continued)

FOREIGN PATENT DOCUMENTS

DE 3108766 9/1982

(Continued)

OTHER PUBLICATIONS

"Cross-Hairs Kit", *Elekta Instruction for Use Brochure*, (2000), pp. 2-5.

(Continued)

*Primary Examiner*—Kevin T Truong
(74) *Attorney, Agent, or Firm*—Scott A. Marks; Stephen W. Bauer

(57) ABSTRACT

This document discusses, among other things, examples of a stereotactic apparatus that includes reticles or other imagable locators for confirming placement of an instrument introduced along a desired trajectory. In certain examples, the reticles are re-positionable with respect to the trajectory to permit placement confirmation along different views. In other examples, the reticles are positionable toward or away from a skull.

31 Claims, 16 Drawing Sheets

U.S. PATENT DOCUMENTS

| | | |
|---|---|---|
| 3,672,352 A | 6/1972 | Summers |
| 3,760,811 A | 9/1973 | Andrew et al. |
| 3,893,449 A | 7/1975 | Lee et al. |
| 3,981,079 A | 9/1976 | Lenczycki |
| 4,013,080 A | 3/1977 | Froning |
| 4,040,427 A | 8/1977 | Winnie |
| 4,230,117 A | 10/1980 | Anichkov ............... 128/303 B |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry ......................... 128/630 |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. ............... 128/303 B |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown .................. 128/303 B |
| 4,617,925 A | 10/1986 | Laitinen ................. 128/303 B |
| 4,618,978 A | 10/1986 | Cosman |
| 4,629,451 A | 12/1986 | Winters et al. |
| 4,638,798 A | 1/1987 | Shelden et al. .......... 128/303 B |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda ................... 128/303 B |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,805,615 A | 2/1989 | Carol ..................... 128/303 B |
| 4,805,634 A | 2/1989 | Ullrich et al. |
| 4,807,620 A | 2/1989 | Strul et al. |
| 4,809,694 A | 3/1989 | Ferrara ...................... 128/303 |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon ..................... 606/130 |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol ........................ 606/130 |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. ............... 128/653 R |
| 5,030,223 A | 7/1991 | Anderson et al. ........... 606/130 |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,078,140 A | 1/1992 | Kwoh ..................... 128/653.1 |
| 5,078,142 A | 1/1992 | Siczek et al. |
| 5,080,662 A | 1/1992 | Paul ......................... 606/130 |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist .................. 606/130 |
| 5,116,345 A | 5/1992 | Jewell et al. ............... 606/130 |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. ............... 606/130 |
| 5,163,430 A | 11/1992 | Carol ..................... 128/653.1 |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson ..................... 606/130 |
| 5,207,223 A | 5/1993 | Adler |
| 5,207,688 A | 5/1993 | Carol ........................ 606/130 |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,246,448 A | 9/1993 | Chang ..................... 606/130 |
| 5,257,998 A | 11/1993 | Ota et al. ................... 606/130 |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. ................ 128/782 |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. ............. 606/130 |
| 5,305,203 A | 4/1994 | Raab et al. |
| 5,306,272 A | 4/1994 | Cohen et al. |
| 5,309,913 A | 5/1994 | Kormos et al. |
| 5,330,485 A | 7/1994 | Clayman et al. ............. 606/130 |
| 5,354,283 A | 10/1994 | Bark et al. ................. 604/180 |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz .................. 128/653.1 |
| 5,387,220 A | 2/1995 | Pisharodi |
| 5,394,457 A | 2/1995 | Leibinger et al. |
| 5,405,330 A | 4/1995 | Zunitch et al. |
| 5,423,848 A | 6/1995 | Washizuka et al. |
| 5,445,166 A | 8/1995 | Taylor |
| 5,452,720 A | 9/1995 | Smith et al. |
| 5,464,446 A | 11/1995 | Dreessen et al. |
| 5,470,307 A | 11/1995 | Lindall |
| 5,474,564 A | 12/1995 | Clayman et al. ............. 606/130 |
| 5,483,961 A | 1/1996 | Kelly et al. ............... 128/653.1 |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. ............. 128/653.1 |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. ............. 128/653.1 |
| 5,575,798 A | 11/1996 | Koutrouvelis ............... 606/130 |
| 5,618,288 A | 4/1997 | Calvo ....................... 606/130 |
| 5,622,170 A | 4/1997 | Schulz |
| 5,638,819 A | 6/1997 | Manwaring et al. |
| 5,643,286 A | 7/1997 | Warner et al. ............... 606/130 |
| 5,647,361 A | 7/1997 | Damadian |
| 5,649,936 A | 7/1997 | Real |
| 5,658,272 A | 8/1997 | Hasson ....................... 606/1 |
| 5,662,600 A | 9/1997 | Watson et al. |

| Patent No. | Date | Inventor | Ref. |
|---|---|---|---|
| 5,667,514 A | 9/1997 | Heller | |
| 5,695,501 A | 12/1997 | Carol et al. | 606/130 |
| 5,713,858 A | 2/1998 | Heruth et al. | |
| 5,755,697 A | 5/1998 | Jones et al. | |
| 5,776,064 A | 7/1998 | Kalfas et al. | |
| 5,776,143 A | 7/1998 | Adams et al. | |
| 5,776,144 A | 7/1998 | Leysieffer et al. | 606/130 |
| 5,788,713 A | 8/1998 | Dubach et al. | |
| 5,807,033 A | 9/1998 | Benway | |
| 5,810,712 A | 9/1998 | Dunn | 600/114 |
| 5,817,106 A | 10/1998 | Real | 606/130 |
| 5,823,975 A | 10/1998 | Stark et al. | |
| 5,833,627 A | 11/1998 | Shmulewitz et al. | 600/562 |
| 5,843,150 A | 12/1998 | Dreessen et al. | |
| 5,851,183 A | 12/1998 | Bucholz | |
| 5,865,817 A | 2/1999 | Moenning et al. | |
| 5,865,842 A | 2/1999 | Knuth et al. | |
| 5,871,445 A | 2/1999 | Bucholz | |
| 5,871,487 A | 2/1999 | Warner et al. | |
| 5,873,822 A | 2/1999 | Ferre et al. | |
| 5,891,034 A | 4/1999 | Bucholz | |
| 5,891,157 A | 4/1999 | Day et al. | 606/130 |
| 5,927,277 A | 7/1999 | Baudino et al. | |
| 5,950,629 A | 9/1999 | Taylor et al. | |
| 5,954,687 A | 9/1999 | Baudino | |
| 5,957,933 A | 9/1999 | Yanof et al. | |
| 5,957,934 A | 9/1999 | Rapoport et al. | |
| 5,964,705 A | 10/1999 | Truwit et al. | |
| 5,980,535 A | 11/1999 | Barnett et al. | 606/130 |
| 5,984,930 A | 11/1999 | Maciunas et al. | 606/130 |
| 5,993,463 A | 11/1999 | Truwit | 606/130 |
| 6,006,126 A | 12/1999 | Cosman | 600/426 |
| 6,018,094 A | 1/2000 | Fox | |
| 6,021,343 A | 2/2000 | Foley et al. | 600/429 |
| 6,024,729 A | 2/2000 | Dehdashtian et al. | |
| 6,039,725 A | 3/2000 | Moenning et al. | |
| 6,044,304 A | 3/2000 | Baudino | |
| 6,058,323 A | 5/2000 | Lemelson | |
| 6,071,288 A | 6/2000 | Carol et al. | 606/130 |
| 6,076,008 A | 6/2000 | Bucholz | |
| 6,079,681 A | 6/2000 | Stern et al. | |
| 6,110,182 A | 8/2000 | Mowlai-Ashtiani | 606/130 |
| 6,117,143 A | 9/2000 | Hynes et al. | 606/130 |
| 6,120,465 A | 9/2000 | Guthrie et al. | |
| 6,135,946 A | 10/2000 | Konen et al. | |
| 6,179,826 B1 | 1/2001 | Aebischer et al. | 604/522 |
| 6,195,577 B1 | 2/2001 | Truwit et al. | |
| 6,206,890 B1 | 3/2001 | Truwit | |
| 6,210,417 B1 | 4/2001 | Baudino et al. | |
| 6,231,526 B1 | 5/2001 | Taylor et al. | |
| 6,236,875 B1 | 5/2001 | Bucholz et al. | |
| 6,254,532 B1 | 7/2001 | Paolitto et al. | |
| 6,257,407 B1 | 7/2001 | Truwit et al. | |
| 6,261,300 B1 | 7/2001 | Carol et al. | 606/130 |
| 6,267,769 B1 | 7/2001 | Truwit | 606/130 |
| 6,267,770 B1 | 7/2001 | Truwit | |
| 6,273,896 B1 * | 8/2001 | Franck et al. | 606/130 |
| 6,282,437 B1 | 8/2001 | Franck et al. | |
| 6,290,644 B1 | 9/2001 | Green, II et al. | |
| 6,298,262 B1 | 10/2001 | Franck et al. | 600/426 |
| 6,315,770 B1 | 11/2001 | de la Torre et al. | |
| 6,321,104 B1 | 11/2001 | Gielen et al. | |
| 6,327,491 B1 | 12/2001 | Franklin et al. | 600/429 |
| 6,356,792 B1 | 3/2002 | Errico et al. | |
| 6,368,329 B1 | 4/2002 | Truwit | |
| 6,457,963 B1 | 10/2002 | Tawara et al. | |
| 6,482,182 B1 | 11/2002 | Carroll et al. | |
| 6,491,699 B1 | 12/2002 | Henderson et al. | |
| 6,529,765 B1 | 3/2003 | Franck et al. | 600/427 |
| 6,537,232 B1 | 3/2003 | Kucharczyk et al. | |
| 6,546,279 B1 | 4/2003 | Bova et al. | |
| 6,547,795 B2 | 4/2003 | Schneiderman | |
| 6,556,857 B1 | 4/2003 | Estes et al. | |
| 6,609,020 B2 | 8/2003 | Gill et al. | |
| 6,610,100 B2 | 8/2003 | Phelps et al. | |
| 6,632,184 B1 | 10/2003 | Truwit | |
| 6,662,035 B2 | 12/2003 | Sochor | |
| 6,676,669 B2 * | 1/2004 | Charles et al. | 606/130 |
| 6,706,050 B1 | 3/2004 | Giannadakis | |
| 6,726,678 B1 | 4/2004 | Nelson et al. | |
| 6,746,471 B2 | 6/2004 | Mortier et al. | |
| 6,752,812 B1 | 6/2004 | Truwit | |
| 6,773,443 B2 | 8/2004 | Truwit et al. | |
| 6,782,288 B2 | 8/2004 | Truwit et al. | |
| 6,802,323 B1 | 10/2004 | Truwit et al. | |
| 6,902,569 B2 | 6/2005 | Parmer et al. | |
| 6,913,478 B2 | 7/2005 | Lamirey et al. | |
| 6,944,895 B2 | 9/2005 | Truwit | |
| 6,960,216 B2 | 11/2005 | Kolb et al. | |
| 2001/0014771 A1 | 8/2001 | Truwit et al. | |
| 2001/0027271 A1 | 10/2001 | Franck et al. | 600/426 |
| 2001/0037524 A1 | 11/2001 | Truwit | |
| 2002/0010479 A1 | 1/2002 | Skakoon et al. | |
| 2002/0019641 A1 | 2/2002 | Truwit | |
| 2002/0022847 A1 | 2/2002 | Ray et al. | |
| 2002/0052610 A1 | 5/2002 | Skakoon et al. | |
| 2002/0077646 A1 | 6/2002 | Truwit et al. | |
| 2002/0156372 A1 | 10/2002 | Skakoon et al. | |
| 2003/0079287 A1 | 5/2003 | Truwit | |
| 2003/0187351 A1 | 10/2003 | Franck et al. | |
| 2004/0059260 A1 | 3/2004 | Truwit | |
| 2004/0176750 A1 | 9/2004 | Nelson et al. | |
| 2004/0243147 A1 | 12/2004 | Lipow | |
| 2004/0255991 A1 | 12/2004 | Truwit et al. | |
| 2004/0260323 A1 | 12/2004 | Truwit et al. | |
| 2004/0267284 A1 | 12/2004 | Parmer et al. | |
| 2006/0192319 A1 | 8/2006 | Solar | |
| 2006/0195119 A1 | 8/2006 | Mazzocchi et al. | |
| 2007/0250078 A1 | 10/2007 | Stuart | |
| 2007/0299427 A1 | 12/2007 | Yeung et al. | |
| 2008/0004632 A1 | 1/2008 | Sutherland et al. | |

FOREIGN PATENT DOCUMENTS

| | | |
|---|---|---|
| DE | 3937052 | 5/1990 |
| DE | 29612100 | 9/1996 |
| DE | 19726141 | 1/1999 |
| DE | 19826078 | 8/1999 |
| DE | 19808220 | 9/1999 |
| DE | 19820808 | 11/1999 |
| EP | 0386936 | 5/1990 |
| EP | 0427358 | 5/1991 |
| EP | 0609085 | 8/1994 |
| EP | 0724865 | 8/1996 |
| EP | 0832611 | 4/1998 |
| EP | 0904741 | 3/1999 |
| GB | 2237993 | 5/1991 |
| GB | 2329473 | 3/1999 |
| GB | 2346573 | 8/2000 |
| WO | WO-8809151 | 12/1988 |
| WO | WO-95/22297 | 8/1995 |
| WO | WO-96/10368 | 4/1996 |
| WO | WO-9633766 | 10/1996 |
| WO | WO-97/03609 | 2/1997 |
| WO | WO-9721380 | 6/1997 |
| WO | WO-9742870 | 11/1997 |
| WO | WO-98/17191 | 4/1998 |
| WO | WO-98/25535 | 6/1998 |
| WO | WO-9851229 | 11/1998 |
| WO | WO-00/01316 | 1/2000 |
| WO | WO-0018306 | 4/2000 |
| WO | WO-0124709 | 4/2001 |
| WO | WO-01/49197 A1 | 7/2001 |

| WO | WO-01/76498 | 10/2001 |

OTHER PUBLICATIONS

"CRW™—Tyco Healthcare Radionics", *Tyco Product Brochure*, pp. 1-7.
"Fathom Remote Introducer", *Image-Guided Neurologics, Inc.*, CNS Hynes Convention Center, (Oct. 30-Nov. 4, 1999), pp. 1-2.
"Leksell Sterotatic System", *Elekta Product Brochure*, pp. 1-6.
Franck, Joel, et al., "microTargeting$^R$ Platform System incorporating StarFixTM guidance", *microTargeting*, (2001-2002), pp. 1-44.
Frank, Joel, et al., "The microTargeting$^R$ Platform Planning Software with STarFix Guidance System", *microTargeting Platform—Incorporating StarFix guidance*, FHC Inc.; L022/Cat. pp. 67-69 150202.
Grady, M., et al., "Nonlinear Magnetic Stereotaxis: Three-Dimensional, in vivo Remote Magnetic Manipulation of a Small Object in Canine Brain", *Medical Physics*, 17 (3), (May/Jun. 1990), pp. 405-415.
Hirschberg, Henry, et al., "Image-guided neurosurgery", *stereotactic equipment for MR imaging*, http://www.medinnova.no/English/P51466ster.html, 1 Page, (viewed web site on Mar. 8, 2002).
Hirschberg, H., et al., "Image-guided neurosurgery—MR compatible stereotactic equipment", http:www.medinnova.no/English/P51466ster.html, p. 1 (viewed web site on Mar. 29, 2001).
Leggett, W. B., et al., "Surgical Technology—The Viewing Wand: A New System for Three-Dimensional Computed Tomography-Correlated Intraoperative Localization", *Current Surgery*, (Dec. 1991), pp. 674-678.
Yeh, H.-S., et al., "Implantation of intracerebral depth electrodes for monitoring seizures using the Pelorus stereotactic system guided by magnetic resonance imaging", *J. Neurosurg*, vol. 78, (1993), pp. 138-141.
Zinreich, S. J., et al., "Frameless Sterotaxic Integration of CT Imaging Data: Accuracy and Initial Applications", *Radiology*, 188 (3), (1993), pp. 735-742.
"Inomed Competence in Neurophysiologic Monitoring", http://www.inomed.com/english/index.htm, (observed Mar. 23, 2004), 2 pgs.
"MicroTargeting® Precision Guidance Using Microelectrode Recording", (Aug. 15, 2003), 5 pgs.
"Possible Existence of Common Internalization Mechanisms among Arginine-rich Peptides", Suzuki, T. et al., Journal of Biological Chemistry, vol. 277, No. 4 (2002) pp. 2437-2443.
Allison, S., et al., "Microchannel Plate Intensifier Response in Traverse Magnetic Field", Electronic Letters, 26, (Jun. 7, 1990), 770-771.
Drake, J. M., et al., "ISG Viewing Wand System", *Neurosurgery*, 34 (6), (Jun. 1994), pp. 1094-1097.
Dyer, P. V., et al., "The ISG Viewing Wand: an application to atlantoaxial surgery using the Le Fort I maxillary osteotomy", *British Journal of Oral & Maxillofacial Surgery*, 33, (1995), pp. 370-374.
Gehring, W. J., "Homeodomain Proteins", Annu. Rev. Biochem., vol. 63 (1997) pp. 487-526.
Gillies, G., et al., "Magnetic Manipulation Instrumentation for Medical Physics Research", Review of Scientific Instruments, 65 (3), Review Article, (Mar. 1994), 533-562.
Grady, M. S., "Magnetic Stereotaxis System for Neurosurgical Procedures", *Proceedings of the 37th International Instrumentation Symposium*, (May 5-9, 1991), pp. 665-675.
Grady, M. S., et al., "Initial Experimental Results of a New Stereotaxic Hyperthermia System", *American College of Surgeons, Surgical Forum*, vol. XXXIX, *Neurological Surgery*, (1988), pp. 507-509.
Grady, M. S., et al., "Magnetic Stereotaxis: A Technique to Deliver Stereotactic Hyperthermia", *Neurosurgery*, 27 (6), (1990), pp. 1010-1016.
Grady, M. S., et al., "Preliminary experimental investigation of in vivo magnetic manipulation: Results and potential application in hyperthermia", *Medical Physics*, 16 (2), (Mar./Apr. 1989), pp. 263-272.
Hata, N., et al., "Needle Insertion Manipulator for CT- and MR-Guided Stereotactic Neurosurgery", *Interventional MR: Techniques and Clinical Experience*, St. Louis : London : Mosby ; Martin Dunitz, F. Jolesz and I. Young, eds., (1998), pp. 99-106.
Howard III, M. A., et al., "Magnetic Neurosurgery: Image-Guided Remote-Controlled Movement of Neurosurgical Implants", *Clinical Neurosurgery*, (1995), pp. 382-391.
Howard III, M. A., et al., "Review of Magnetic Neurosurgery Research", *Journal of Image Guided Surgery*, 1 (6), (1995), pp. 295-299.
Howard, M. A., et al., "Magnetic Movement of a Brain Thermoceptor", *Neurosurgery*, 24 (3), (Mar. 1989), pp. 444-448.
Howard, M. A., et al., "Magnetic Neurosurgery", Proceedings of the Meeting of the American Society for Stereotactic and Functional Neurosurgery, (Mar. 8-11, 1995), pp. 102-107.
Lawson, M. A., et al., "Near Real-Time Bi-planar Fluoroscopic Tracking System for the Video Tumor Fighter", *SPIE*, vol. 1445 *Image Processing*, (1991), pp. 265-275.
Malison, R. T., et al., "Computer-Assisted Coregistration of Multislice SPECT and MR Brain Images by Fixed External Fiducials", Journal of Computer Assisted Tomography, 17 (6) (1993) pp. 952-960.
Mannervik, M., "Target genes of homeodomain proteins", BioEssays vol. 21.4 (Apr. 1999) pp. 267-270.
McNeil, R. G., et al., "Characteristics of an Improved Magnetic-Implant Guidance System", *IEEE Transactions on Biomedical Engineering*, 42 (8), (Aug. 1995), pp. 802-808.
McNeil, R. G., et al., "Functional Design Features and Initial Performance Characteristics of a Magnetic-Implant Guidance System for Stereotactic Neurosurgery", *IEEE Transactions on Biomedical Engineering*, 42 (8), pp. 793-801.
Meeker, D., et al., "Optimal Realization of Arbitrary Forces in a Magnetic Stereotaxis System," IEEE Transactions on Magnetics, 32 (2), (Mar. 1996), 320-328.
Molloy, J. A., et al., "Experimental Determination of the Force Required for Insertion of a Thermoseed Into Deep Brain Tissues", *Annals of Biomedical Engineering*, 18 (3), (1990), pp. 299-313.
Molloy, J. A., et al., "Thermodynamics of movable inductively heated seeds for the treatment of brain tumors", *Medical Physics*, 18 (4), (Jul./Aug. 1991), pp. 794-803.
Oliver, L., "Cup-And-Ball Chemopallidectomy Apparatus", (1958), p. 401.
Patikoglou, G. et al., "Eukaryotic Transcription Factor-DNA Complexes", Annual Review of Biophysics and Biomolecular Structure vol. 26 (1997) pp. 289-325.
Quate, E., et al., "Goniometric Motion Controller for the Superconducting Coil in a Magnetic Stereotaxis System", IEEE Transactions on Biomedical Engineering, 38 (9), (Sep. 1991), 899-905.
Ramos, P. A., et al., "Electro-optic imaging chain for a biplanar fluoroscope for neurosurgery: magnetic field sensitivity and contrast measurements", *Optical Engineering*, 32 (7), (Jul. 1993), pp. 1644-1656.
Ramos, P. A., et al., "Low-dose, magnetic field-immune, bi-planar fluoroscopy for neurosurgery", *SPIE Medical Imaging V: Image Physics*, vol. 1443, (1991), pp. 160-170.
Ramos, P. A., et al., "Microchannel Plate Image Intensifier Electron Dynamics in Magnetic Field", *Electronics Letters*, 27 (18), (Aug. 29, 1991), pp. 1636-1638.
Ritter, R. C., et al., "Magnetic Stereotaxis: An Application of Magnetic Control Technology to the Needs of Clinical Medicine", *Proc. Of the MAG'95 Industrial Conf. and Exhibition*, Technomic Pub. Co., Lancaster, PA., Allaire, P., ed., (1995), pp. 186-193.
Ritter, R. C., et al., "Magnetic Stereotaxis: Computer-Assisted Image-Guided Remote Movement of Implants in the Brain", *Computer-Integrated Surgery: Technology and Clinical Applications*, MIT Press, (1996), pp. 363-369.
Sandeman, D. S., et al., "Advances in image-directed neurosurgery: Preliminary experience with the ISG Viewing Wand compared with the Leksell G frame", *British Journal of Neurosurgery*, 8, (1999), pp. 529-544.
Stein, S. et al., "Checklist: Vertebrate homeobox genes", Mechanisms of Development, vol. 55, No. 1 (Mar. 1996) pp. 91-108.

Szikora, Istvan, et al., "Endovascular Treatment of Experimental Aneurysms with Liquid Polymers: The Protective Potential of Stents", *Neurosurgery*, 38 (2), (Feb. 1996), pp. 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

International Search Report and Written Opinion for PCT/US05/43651 mailed May 8, 2008.

* cited by examiner

TARGET DEPTH LOCATORS FOR TRAJECTORY GUIDE FOR INTRODUCING AN INSTRUMENT

FIELD OF THE INVENTION

This document relates generally to trajectory guides for steering an instrument, and more specifically, but not by way of limitation, to target depth locators for a trajectory guide.

BACKGROUND

Neurosurgery sometimes involves inserting an instrument through a burr hole or other entry portal into a subject's brain toward a target region of the brain. Because of the precision needed to reach the target, while avoiding nearby structures that are often critical to brain function, stereotactic instrument guidance is sometimes provided. In one such technique, a stereotactic headframe is mounted about the patient's skull. A trajectory guide is mounted to the headframe to provide an instrument-guiding trajectory through the burr hole and aimed toward the target. In another technique (sometimes referred to as "frameless stereotaxy"), a trajectory guide is locally mounted directly to the skull in or about the burr hole. The skull-mounted trajectory guide also provides an instrument-guiding trajectory through the burr hole and aimed toward the target. In either technique, an image-guided workstation may be used to provide navigational guidance to the neurosurgeon, such as by displaying preoperative images of the subject to assist the neurosurgeon in planning or performing the procedure.

Among other things, the present inventors have recognized that a neurosurgeon using a trajectory guide to introduce an instrument to a target may want to confirm that the instrument has actually reached the depth of the desired target. For these and other reasons, which will become apparent upon reading the following detailed description and viewing the drawings that form a part thereof, the present inventors have recognized an unmet need for trajectory guide systems, devices, and methods allow confirmation that an instrument being introduced has actually reached the desired target.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
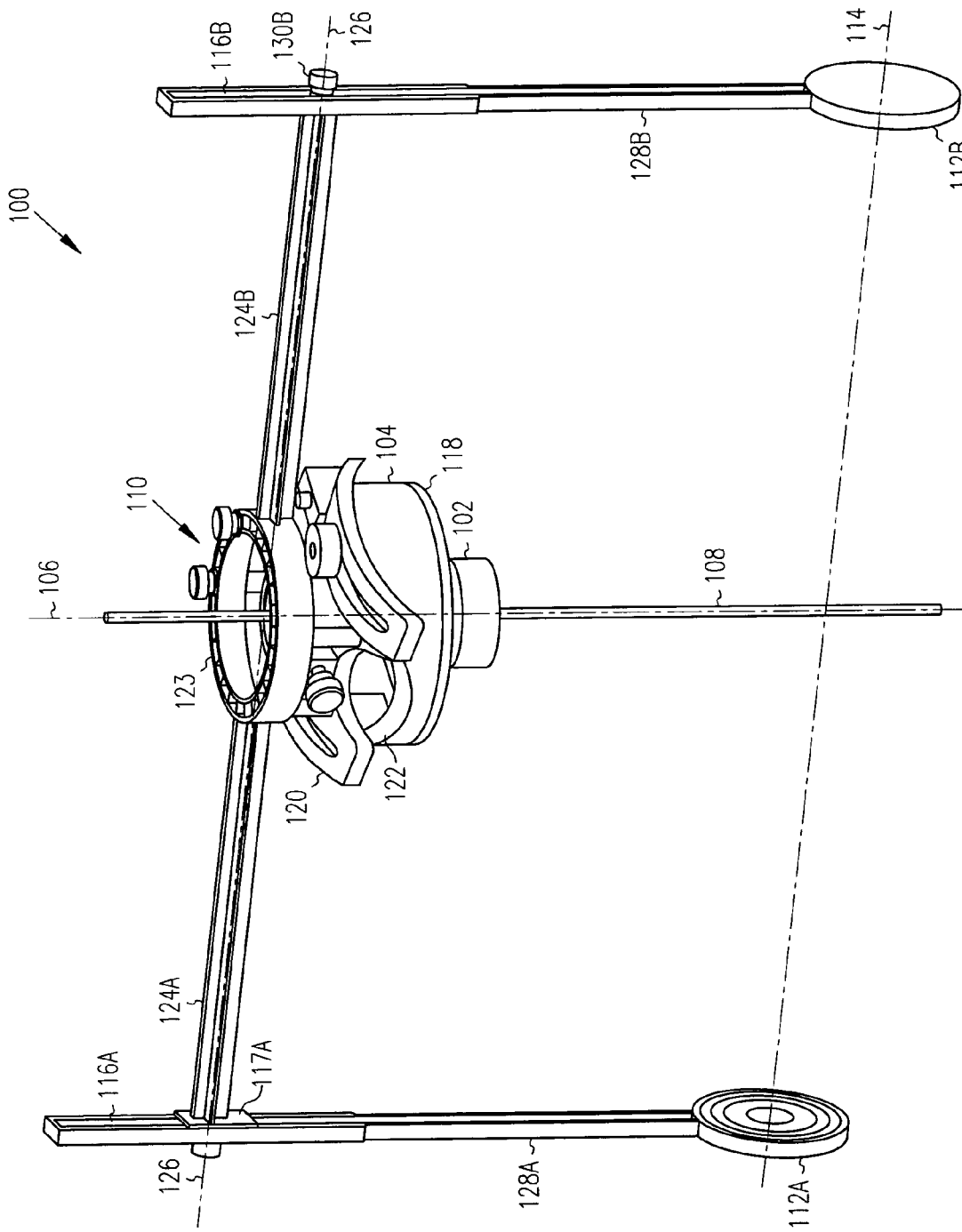
FIG. 1 is a perspective view schematic diagram illustrating generally an example of portions of a stereotactic apparatus.

FIG. 1 is a perspective view schematic diagram illustrating generally, by way of example, but not by way of limitation, portions of a stereotactic apparatus 100. In this example, the stereotactic apparatus 100 includes a mounting base 102 and a trajectory guide assembly 104 coupled to the mounting base 102. The mounting base 102 is configured, in this example, to be secured in or about a burr hole in a subject's skull (or in or about another entry portal in another surface of an animate or inanimate object). In this example, the trajectory guide assembly 104 is adjustably orientable with respect to the mounting base 102. The trajectory guide assembly 104 provides an adjustably orientable trajectory 106. Along this trajectory 106, a catheter, an electrode, or another instrument 108 is guided through the entry portal toward a target located beyond the surface. A positioning assembly 110 is coupled to the trajectory guide assembly 104. In this example, the positioning assembly 110 carries imagable locators, such as imagable reticles 112A-B (also referred to as "reticules"). Such imagable locators are used for confirming, using an imaging system to locate the locators, that the instrument 108 introduced along the trajectory 106 has reached a desired depth or other desired location corresponding to a desired target. Examples of suitable imaging systems include, by way of example, but not by way of limitation, magnetic resonance (MR) imaging systems, computed tomography (CT), positron emission tomography (PET), and single photon emission computed tomography (SPECT), X-ray, fluoroscopy, or other radiographic imaging systems, ultrasonic imaging systems, and the like.

In this example, the positioning assembly 110 is coupled to the trajectory guide assembly 104 such that a "sighting" line 114, conceptually defined between centers of reticles 112A-B. The sighting line 114 intersects the trajectory 106—even as the trajectory guide assembly 104 is adjusted, with respect to the fixed mounting base 102, to orient the trajectory 106. In this example, the positioning assembly 110 further includes at least one positioner, such as scaled slots 116A-B. A scale accompanying each of the respective slots 116A-B includes viewable indicia providing depth information.

The slots 116A-B permit adjustment of the locations of the reticles 112A-B such that the sighting line 114 can be adjusted to intersect the trajectory 106 at different points. In one example, the sighting line 114 is adjusted to intersect the trajectory 106 at a depth that corresponds to a desired target location in the subject's brain. Thus, by "sighting" along sighting line 114 (i.e., using the imaging system), the user can confirm whether the instrument 108 has reached the desired target depth, along the trajectory 106. More particularly, the instrument 108 will have reached the desired target depth along the trajectory 106 when the imaging system detects the tip (or other imagable indicator locatable by the imaging system) on the instrument 108 as being coincident with the sighting line 114.

In the example of FIG. 1, the positioning assembly 110, carrying the reticles 112A-B for confirming the depth of the instrument 108, is coupled to an adjustably orientable trajectory guide assembly 104 that adjusts the trajectory 106 (for introducing the instrument 108) by separately adjusting (1) a rotation about an axis that is concentric and orthogonal to the burr hole or other entry portal in or about which the mounting base 102 is secured, and (2) a tilting of an instrument guide lumen (or lumens) to adjust an angle between the instrument trajectory 106 and the concentric axis. In one example, as illustrated in FIG. 1, the trajectory guide assembly 104 rotatably rides on a platform ring 118, provided by the mounting base 102. This provides the rotational adjustment about the concentric axis. In this example, the trajectory guide assembly 104 further includes a "saddle" 120 riding along a semispheric arc-shaped surface 122. This provides the tilting adjustment of the angle of the trajectory 106 with respect to the concentric axis. One example of portions of a suitable trajectory guide assembly 104 and mounting base 102 is described in Skakoon et al. U.S. patent application Ser. No. 09/828,451 entitled "DEEP ORGAN ACCESS DEVICE AND METHOD," which was filed on Apr. 6, 2001, and which is incorporated herein by reference in its entirety, including its disclosure of trajectory guide structures and methods. In one example, the stereotactic apparatus 100 provides multiple trajectories 106, such as by using a multilumen insert, one example of which is described in the above-incorporated Skakoon et al. U.S. patent application Ser. No. 09/828,451.

In the example of FIG. 1, the positioning assembly 100 is detachably mounted to the trajectory guide assembly 110 using an indexing circular or semicircular ring 123. In FIG. 1, the ring 123 is mounted to the trajectory guide assembly 104 substantially concentrically to the trajectory 106 provided by the trajectory guide assembly 104. In the illustrated example, elongated radial arms 124A-B radially extend out from opposing sides of the outer circumference of the ring 123, such that a line 126 (which is conceptually defined to extend longitudinally through both of the longitudinally-aligned radial arms 124A-B) orthogonally intersects the trajectory 106. In this example, elongated side arms 128A-B extend orthogonally downward from the outer ends (i.e., the ends that are located away from the ring 123 and the trajectory guide assembly 104) of the respective radial arms 124A-B. The side arms 128A-B are oriented, with respect to the respective radial arms 124A-B, such that the side arms 128A-B longitudinally extend parallel to the trajectory 106. In this example, the outer ends (i.e., away from the respective radial arms 124A-B) of the side arms 128A-B carry disk-shaped imagable reticles 112A-B, or other imagable locators. In this example, the side arms 128A-B each include respective slots 116A-B into which sliding end blocks 117A-B of the radial arms 124A-B are inserted. This permits the side arms 128A-B to slide up and down with respect to the radial arms 124A-B, for adjusting the reticles 112A-B toward and away from the radial arms 124A-B. The slots 116A-B include respective depth scales or other indicia. This permits adjustment of reticles 112A-B such that the sighting line 114 corresponds to the desired target depth along the trajectory 106. A locking mechanism, such as thumbscrews 130A-B or the like, extends through each one of the slots 116A-B. This permits this side arms 128A-B to be secured with respect to the radial arms 124A-B. This, in turn, permits the reticles 112A-B to be securely positioned such that the sighting line 114 intersects the trajectory 106 at an appropriate point along the trajectory 106 that corresponds to the desired target depth along the trajectory 106.

In one example of use, with the mounting base 102 locally secured to a subject's skull (e.g., in or about a burr hole in the skull), the radial arms 124A-B and the side arms 128A-B position the reticles 112A-B on opposing sides of the subject's skull, into which the trajectory 106 extends. In a further example, the ring 123 is configured to permit mounting to the trajectory guide assembly 104 in multiple different orientations. This allows repositioning of the reticles 112A-B about the subject's skull. In one such example, the ring 123 is first mounted such that the reticles 112A-B are respectively positioned near the left and right sides of the subject's skull. Target depth/location confirmation is then performed using this first orientation. Then, the ring 123 is re-oriented such that the reticles 112A-B are respectively positioned near the front and back sides of the subject's skull. Target depth/location confirmation is then again performed using this second orientation. However, such first and second orientations need not be orthogonal. Instead, intermediate orientations are also possible, permitting target depth/location confirmation from different "views."

Figure 2:
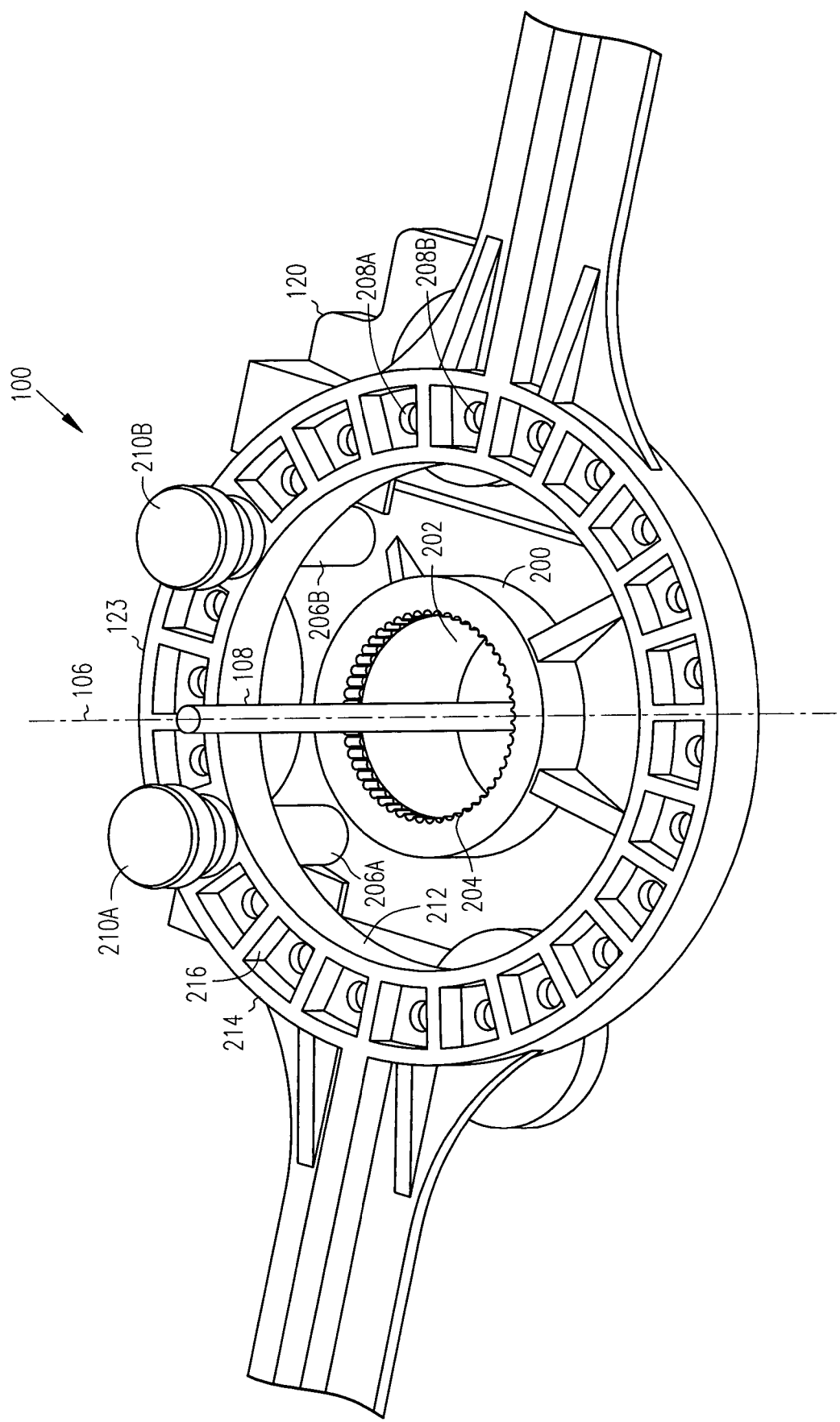
FIG. 2 is a top perspective view illustrating an example of portions of the stereotactic apparatus in more detail.

FIG. 2 is a top perspective view illustrating an example of portions of the stereotactic apparatus 100 in more detail. In this example, the saddle 120 of the trajectory guide assembly 104 includes a stage 200 defining a lumen 202 therethrough. The lumen 202 points at the burr hole or other entry portal from different orientations, which are obtained by adjusting the rotational and tilting degrees of freedom of the trajectory guide assembly 104, as discussed above. The lumen 202 receives a multilumen or other insert (not shown in FIG. 2), which provides at least one instrument guide lumen that constrains the instrument 108 being introduced, thereby defining its trajectory 106. In this example, the lumen 202 includes teeth 204, located on a portion of its internal circumference, for engaging corresponding mating teeth on a portion of the external circumference of the guide-lumen-bearing insert that is inserted into the lumen 202. The teeth 204 permit insertion of the guide-lumen-bearing insert into the lumen 202 in a desired one of a plurality of possible orientations defined by engagement with the teeth 204.

In the example of FIG. 2, the ring 123 is seated on four posts 206A-D (or otherwise seated on any other suitable number of posts or other suitable structures). In this example, the posts 206 are received within respective rims extending downward from the respective internal and external circumferences of the ring 123. This allows the ring 123 to circularly ride upon the posts 206A-D. This riding permits the positioning assembly 110 to be rotated to reposition the reticles 112A-B (e.g., from locations at the front and back of the subject's skull to locations at the left and right sides of the subject's skull, as discussed above).

Figure 3:
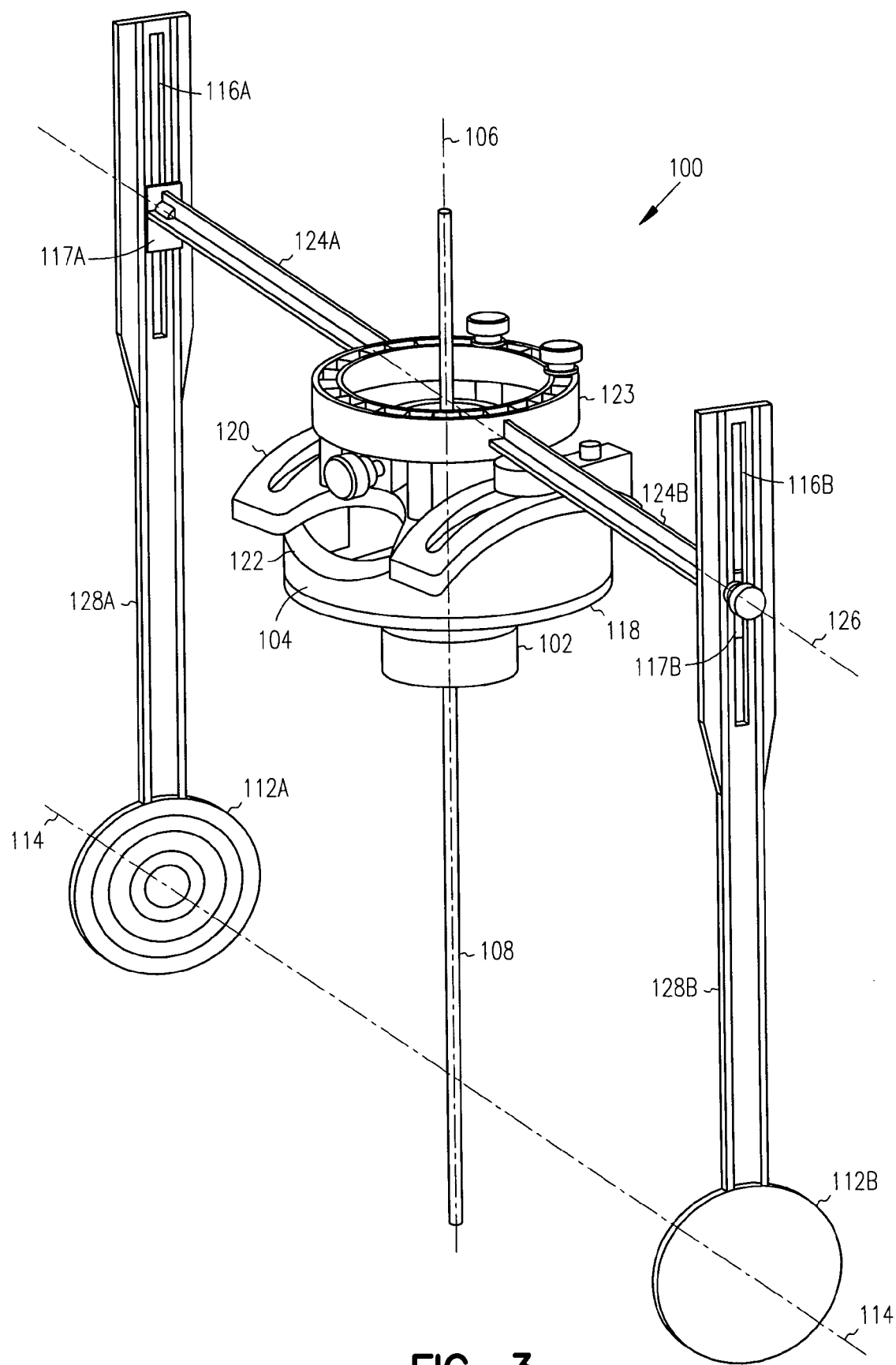
FIG. 3 is a perspective view schematic diagram that illustrates generally an example of the stereotactic apparatus with the positioning assembly re-oriented by 45° with respect to the position illustrated in FIG. 1.

In this example, the ring 123 includes a plurality of through-holes 208 that are distributed about the circumference of the ring 123. Thumbscrews 210A-B extend through selected through-holes 208 to secure the ring 123 to the posts 206 with the positioning assembly 110 in the desired orientation for performing the depth confirmation. To reposition the positioning assembly 110 in a different orientation, the thumbscrews 210A-B are removed and re-inserted into different through-holes 208. FIG. 3 is a perspective view schematic diagram that illustrates an example of the stereotactic apparatus 100 in which the ring 123 has been rotated and repositioned by 45° with respect to the position illustrated in FIG. 1.

In the example illustrated in FIG. 2, the ring 123 includes an inner circumferential rim 212 and an outer circumferential rim 214. The rims 212 and 214 are connected by multiple plates 216. These plates 216 are distributed about the circumference of the ring 123. The plates 216 assist in providing the ring 123 with sufficient mechanical strength for supporting the radial arms 124A-B, the side arms 128A-B, and the reticles 112A-B. Similarly, the radial arms 124A-B include I-beams, braces, or other mechanical support structures. This provides sufficient mechanical strength for supporting and positioning the side arms 128A-B and the reticles 112A-B with the desired degree of accuracy for verifying that the instrument 108 has reached the desired target depth. In one example, the ring 123, the radial arms 124A-B, and the side arms 128A-B are made of acetylbutylstyrene (ABS), polycarbonate, or other rigid plastic material. In one example, such materials permit such components to be MR-compatible, sterilizable, and/or disposable.

Figure 4:
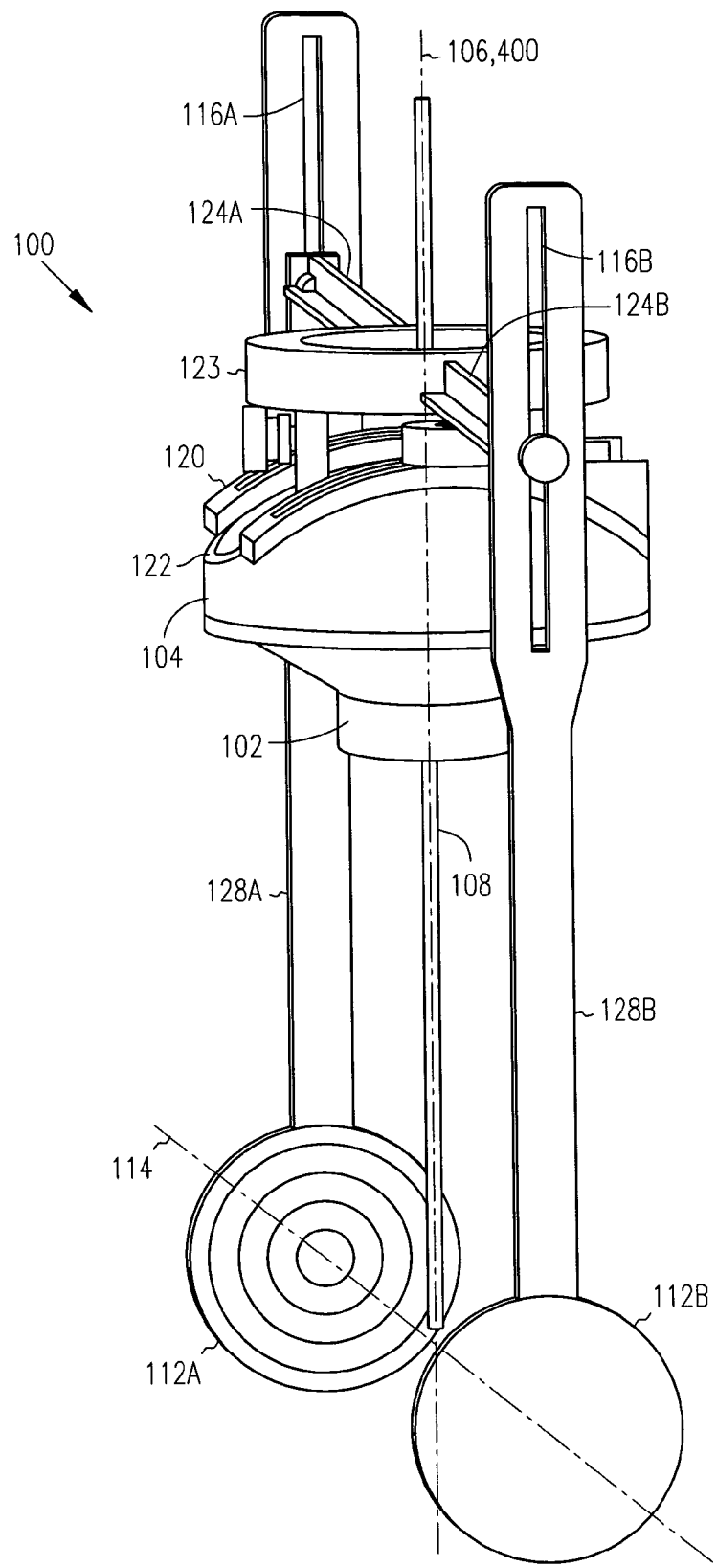
FIG. 4 is a side perspective view schematic diagram illustrating generally an example of portions of the stereotactic apparatus in which the trajectory is coincident with an axis extending substantially concentrically through and orthogonal to a burr hole or other entry portal to or about which a mounting base is secured.

FIG. 4 is a side perspective view schematic diagram illustrating an example of portions of the stereotactic apparatus 100 in which the trajectory 106 is coincident with an axis 400 extending substantially concentrically through and orthogonal to a burr hole or other entry portal to or about which the mounting base 102 is secured. Therefore, in the illustration of FIG. 4, the side arms 128A-B extend longitudinally parallel to both the trajectory 106 and the concentric axis 400. In this illustration, the sighting line 114 intersects both the trajectory 106 and the concentric axis 400.

Figure 5:
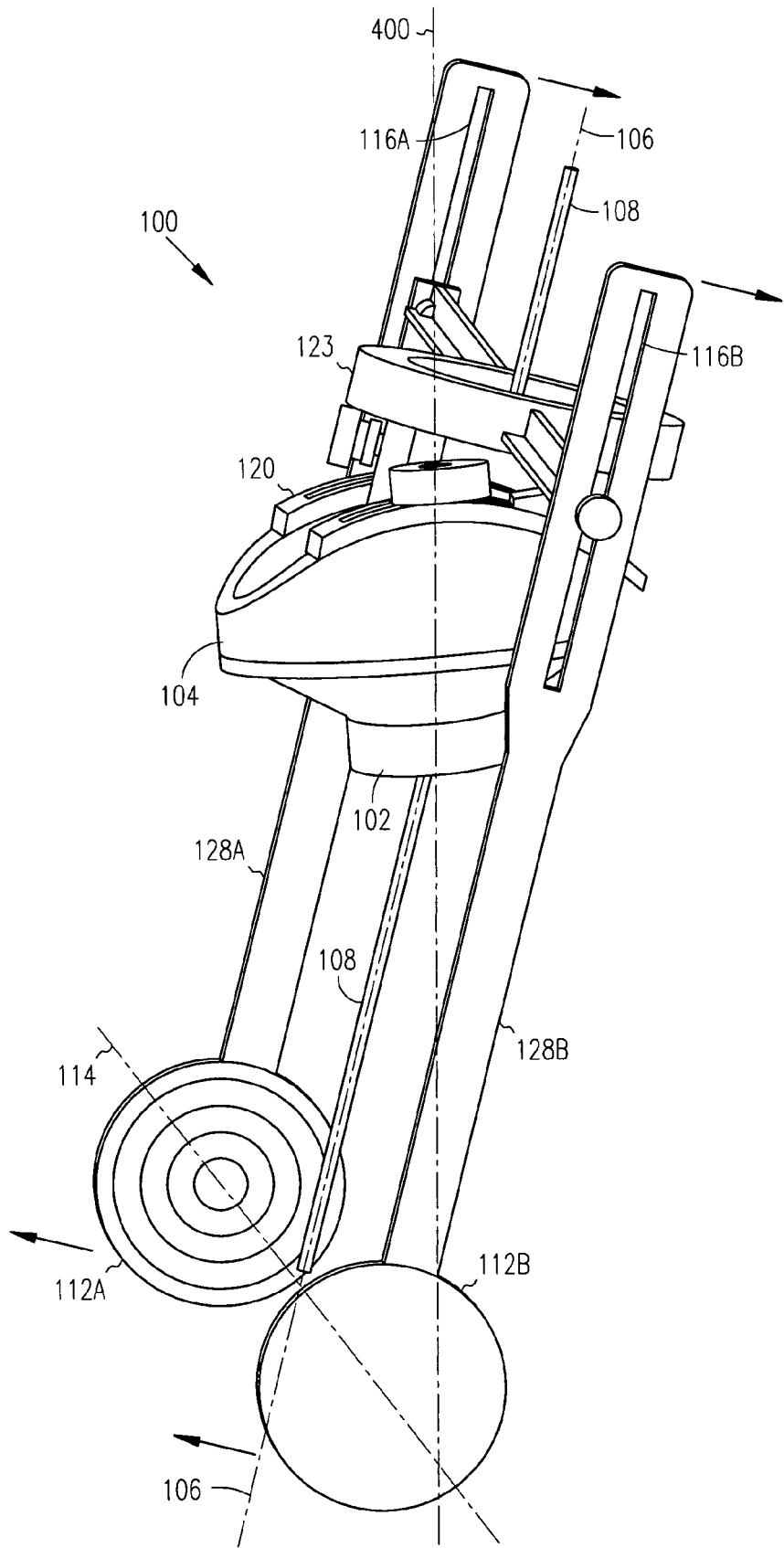
FIG. 5 is a side perspective view schematic diagram illustrating generally an example of portions of the stereotactic apparatus in which the trajectory has been tilted at an angle to an axis extending substantially concentrically through and orthogonal to a burr hole or other entry portal to or about which a mounting base is secured.

By contrast, FIG. 5 is a side perspective view schematic diagram illustrating an example of portions of the stereotactic apparatus 100 in which the trajectory 106 has been tilted (such as by adjusting the position of the saddle 120 on the semispheric arc 122) at an angle to the axis 400. The positioning assembly 110 moves along with the saddle 120 portion of the trajectory guide assembly 104, to which the positioning assembly 104 is attached. Therefore, in the illustration of FIG. 5, the side arms 128A-B continue to extend parallel to the trajectory 106 (e.g., after the saddle 120 is adjusted), but are no longer parallel to the concentric axis 400. Consequently, in this illustration, the sighting line 114 continues to intersect the trajectory 106, but no longer intersects the concentric axis 400. In this manner, sighting line 114 is positioned to confirm depth of the instrument 108 along the trajectory 106, the orientation of which may be adjusted by the user to intersect the desired target located beyond the burr hole or other entry portal in the surface.

Figure 6:
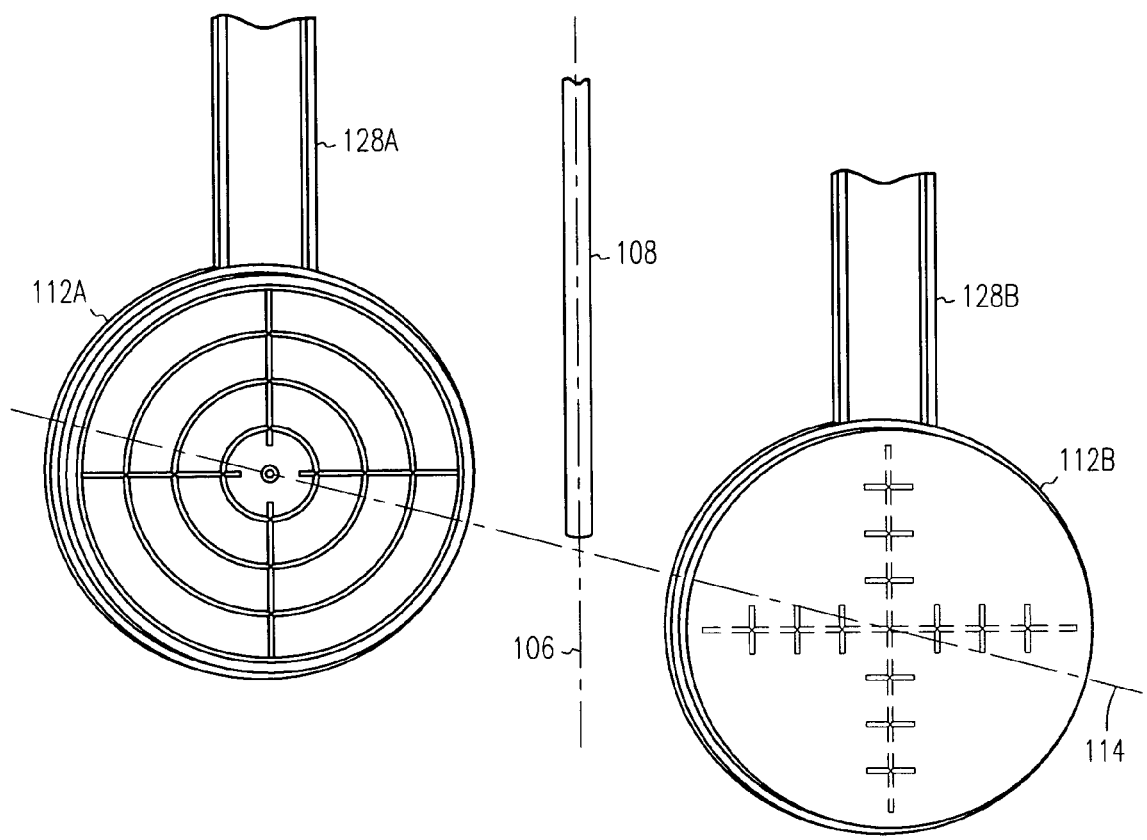
FIG. 6 is a schematic diagram illustrating conceptually a view of reticles and an instrument being introduced along the guided trajectory, such as would be seen on an imaging system used to confirm placement of the instrument at the desired depth along the trajectory.

FIG. 6 is a schematic diagram illustrating conceptually a view of the reticles 112A-B and the instrument 108, such as would be seen on the imaging system that is used to confirm placement of the instrument 108 at the desired depth along the trajectory 106. In the illustration of FIG. 6, each of reticles 112A-B includes an imagable target pattern for assisting the user in "sighting" along the sighting line 114 using the imaging system. In the example illustrated in FIG. 6, the reticle 112A includes a "bullseye" pattern of concentric circles about a centerpoint of the reticle 112A through which the sighting line 114 is defined. These circles are spaced apart at predetermined equal distances. In this example, the reticle 112B includes a different pattern than reticle 112A, thereby allowing the user to distinguish between the two reticles 112A-B using the display of the imaging system. For example, in the illustration of FIG. 6, the reticle 112B includes crosshairs intersecting at a centerpoint of the reticle 112B through which the sighting line 114 is defined. Each crosshair includes orthogonal hashmarks that are spaced at equal predetermined distances from the centerpoint of the reticle 112B at which the crosshairs intersect. The different patterns of reticles 112A-B make it easier for the user to align the centerpoints of the reticles 112A-B to "sight" along sighting line 114 using the imaging system. However, such sighting alignment could also be performed, for example, using a wide variety of other patterns. Such patterns may even constitute using only imagable centerpoint locators (e.g., dots) at the centers of reticles 112A-B. Therefore, neither of imagable reticles 112A-B need require an imagable network or pattern.

In one example, the reticles 112A-B include plastic or other disks (which are substantially invisible on the imaging system display), which include wires, arranged into the patterns carried by the disks. If the reticles 112A-B are intended for use with fluoroscopy or x-ray imaging, then the wires include tungsten, gold, platinum, stainless steel, a dense Noble metal, or other such material providing good radiological image contrast. In various examples, the wires implementing the patterns are molded into the plastic disks, inserted into milled routes in the plastic disks, adhered to the plastic disks, or otherwise affixed to or incorporated in the plastic disks.

In another example, the patterns are printed onto, absorbed into, etched into or otherwise affixed to portions of the plastic or other disks (or onto decals that are adhered thereto). In one such example, these patterns use ink that includes tungsten or similar powder, or that is otherwise formulated to be visible on the imaging system display. In yet a further example, the patterns are multimodal, that is, they are visible on a plurality of different types of imaging systems (e.g., CT and MR, etc.). At least a portion of the instrument 108 (e.g., the instrument tip) is also constructed to be visible on the display of the particular imaging system used for depth confirmation.

In yet another manufacturing example, the reticles 112A-B include grooves that are milled, etched chemically or using a laser or otherwise, or otherwise formed into the plastic disks to form the patterns. In one example, the grooves have a thickness between about 0.025 inches and 0.030 inches. An epoxy is mixed with tungsten powder (or other radiological or other imagable substance). The epoxy mixture is applied to the plastic disks and introduced into the grooves. The excess epoxy mixture is wiped off, leaving behind only the epoxy mixture that was introduced into the grooves. The resulting patterned epoxy mixture is allowed to harden.

Figure 7A:
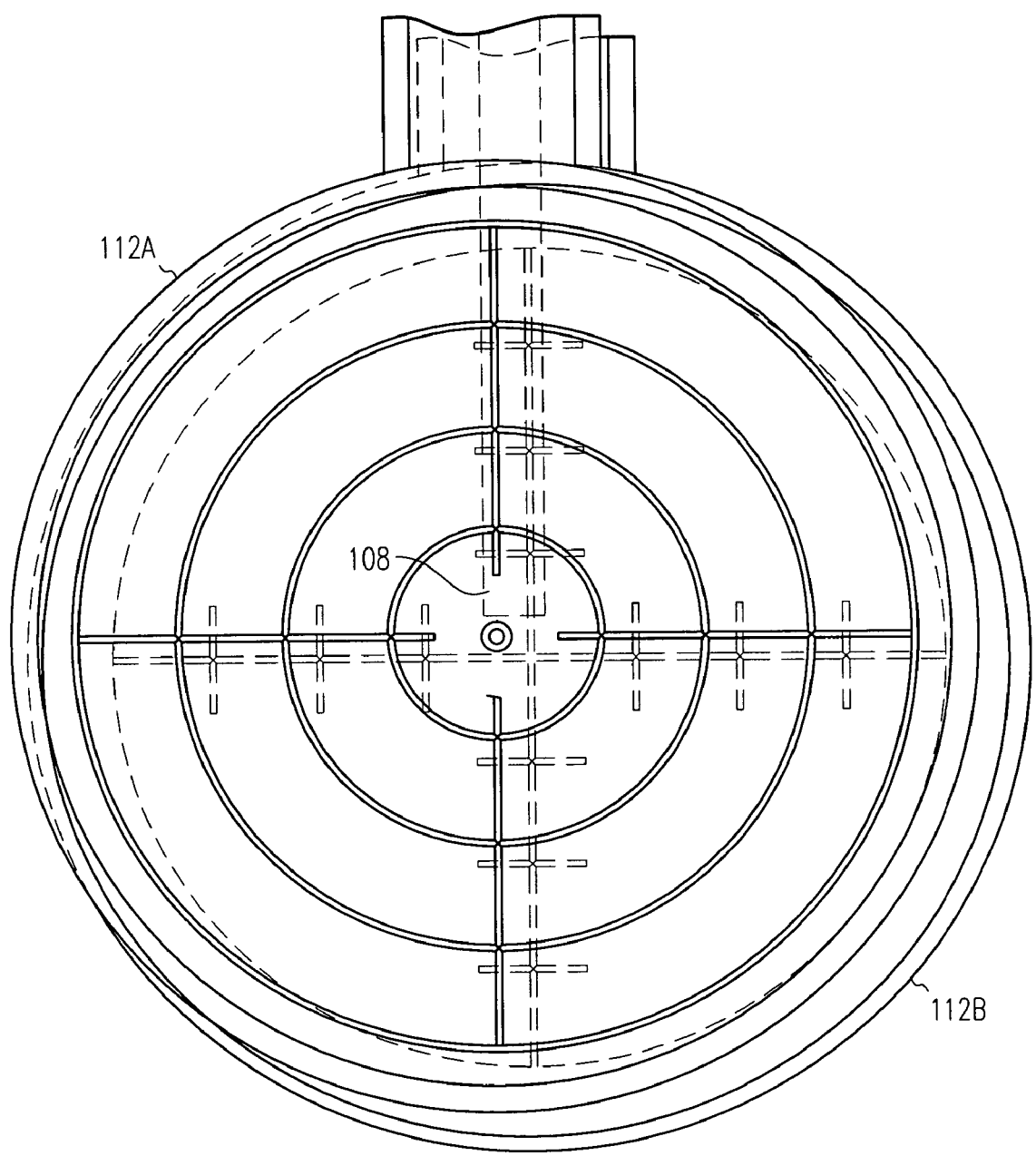
FIG. 7A is a schematic diagram that illustrates conceptually a side view of the reticles and the instrument, such as would be seen on the imaging system confirming placement of the instrument at the desired depth along the trajectory.

FIG. 7A illustrates conceptually a side view of the reticles 112A-B and the instrument 108, such as would be seen on the imaging system that is used to confirm placement of the instrument 108 at the desired depth along the trajectory 106. In this example, the centerpoints of the reticles 112A-B are nearly aligned with each other.

Figure 7B:
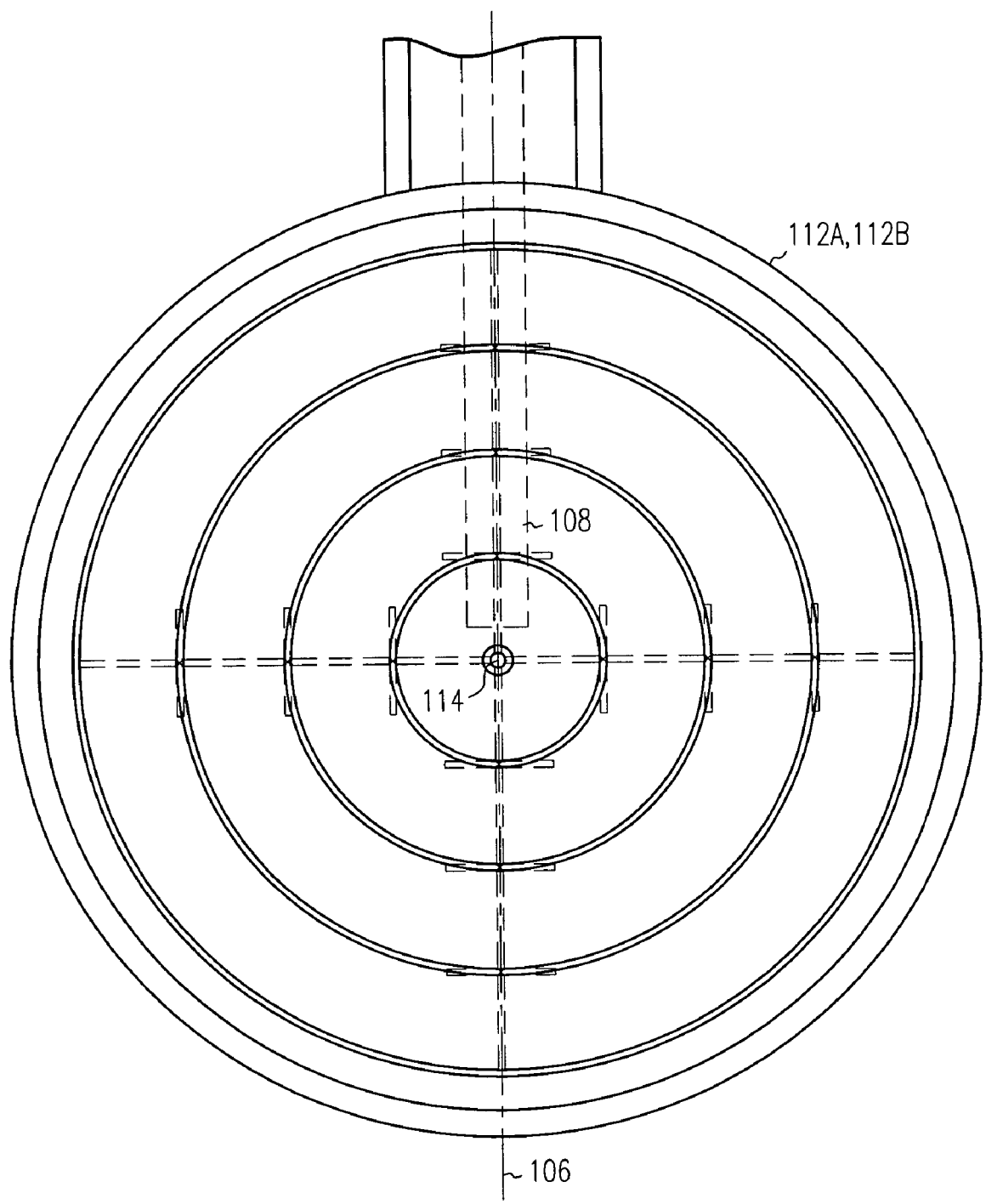
FIG. 7B is a schematic diagram that illustrates conceptually a side view of the reticles and the instrument, such as would be seen on the imaging system confirming placement of the instrument at the desired depth along the trajectory.

FIG. 7B illustrates conceptually a side view of the reticles 112A-B and the instrument 108, such as would be seen on the imaging system that is used to confirm placement of the instrument 108 at the desired depth along the trajectory 106. In this example, the centerpoints of the reticles 112A-B are aligned with each other, thereby conceptually defining the sighting line 114 to extend orthogonally into and out of the page illustrating FIG. 7B. In this example, the concentric circles patterned onto reticle 112A are spaced 10 millimeters apart from each other. Similarly, the hash marks orthogonally intersecting the crosshairs of reticle 112B are also spaced 10 millimeters away from each other.

In the example illustrated in FIG. 7B, the imaging system display indicates that the tip of the instrument 108 being introduced along the trajectory 106 is about 2 millimeters short of the desired target to which the centerpoints of the reticles 112A-B have been adjusted. The user may then insert the instrument 108 along the trajectory 106 an additional two millimeters to bring the tip of the instrument 108 to the point at which the trajectory 106 and the sighting line 114 intersect. However, doing so may still not bring the tip of the instrument 108 to the desired target location in 3D space, since target confirmation has been obtained only along the particular sighting line 114. But, by circularly rotating the positioning apparatus 110 about the trajectory 106 (such as by using the thumbscrews 210A-B and the particularly selected through-holes 208 of the ring 123) depth confirmation can be obtained along one or more other sighting lines 114 intersecting the trajectory 106 from different directions. For example, an instrument 108 having a tip aligned to the first sighting line 114 in FIG. 7B may still be off-target along a second sighting line that is taken orthogonal to the sighting line 114 illustrated in FIG. 7B (e.g., by rotatably repositioning the ring 123), in which case the instrument 108 would appear to the right or left of the commonly aligned centerpoints of the reticles 112A-D along that second sighting line.

Figure 8:
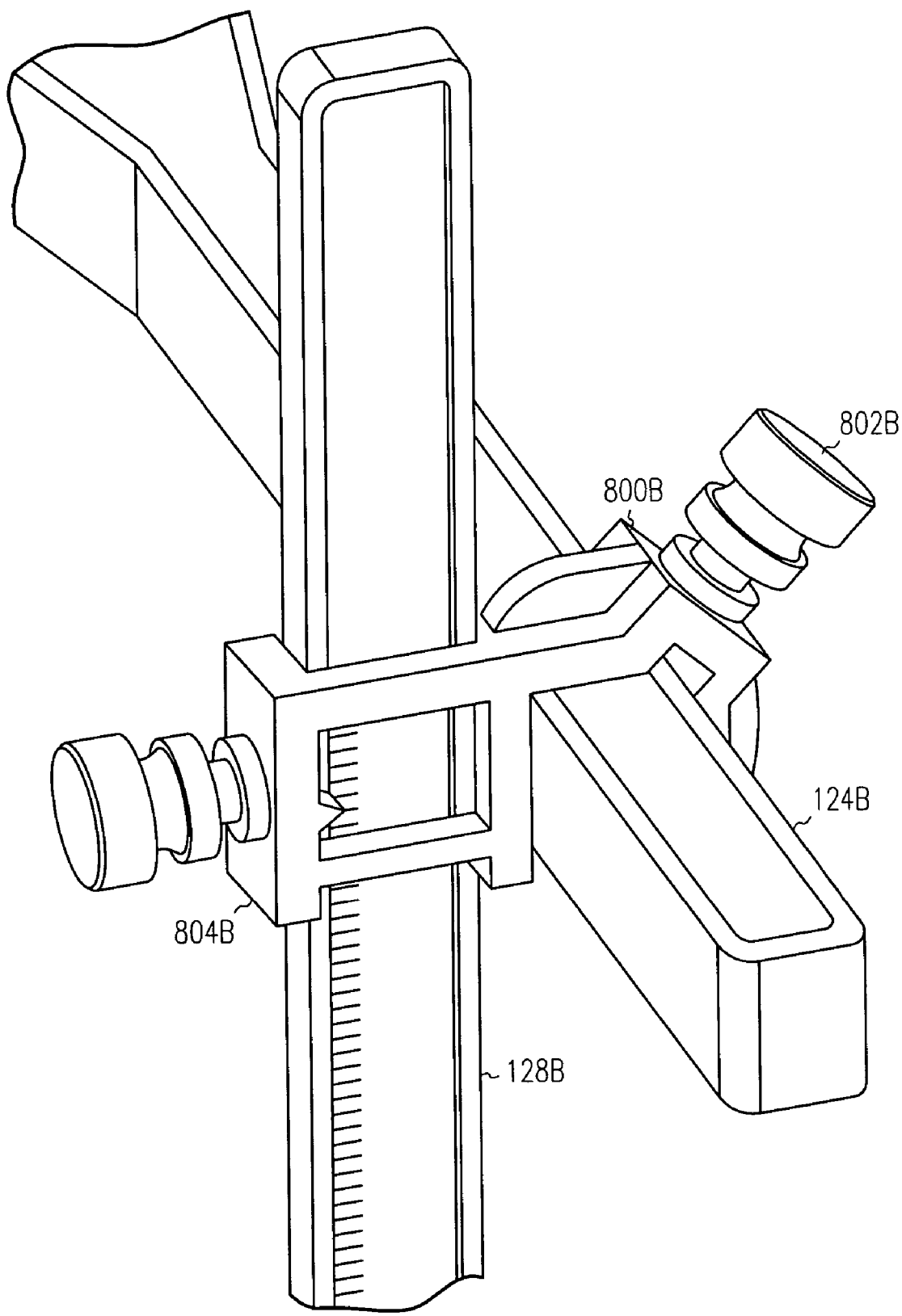
FIG. 8 is a schematic diagram illustrating generally portions of one embodiment of an apparatus in which the side arms are adjustably coupled to the radial arms.

FIG. 8 is a schematic diagram illustrating generally, by way of example, but not by way of limitation, portions of one embodiment of the apparatus 100 in which the side arms 128A-B are adjustably coupled to the radial arms 124A-B. This allows the reticles 112A-B to be moved toward and away from the subject's skull, if desired by the user. In the example illustrated in FIG. 8, a slide 800B rides along the radial arm 124B until secured by a locking device, such as a thumbscrew 802B. Moreover, in the illustrated example, the side arm 128B slides through a guide portion 804B of the slide 800B, thereby allowing depth adjustment of the reticles 112B using a scale on the side arm 128B in conjunction with an indicator 806B on the guide portion 804B of the slide 800B. Although not shown in the close-up view illustrated in FIG. 8, in this embodiment, the opposing side arm 124A and radial arm 128A include a similar slide 800A.

Figure 9:
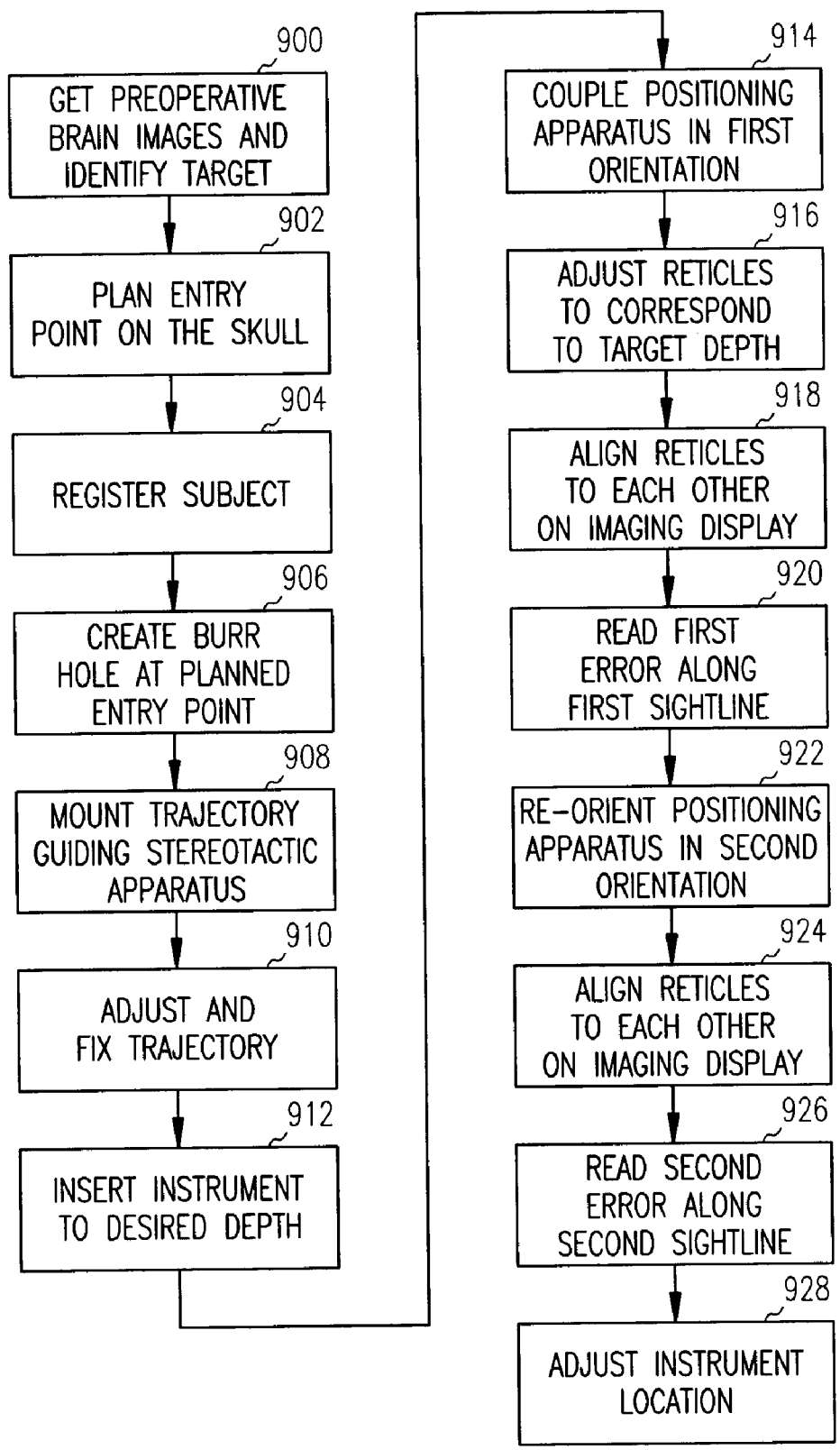
FIG. 9 is a flow chart illustrating generally one example of a technique for performing instrument depth confirmation during an image-guided neurosurgery procedure.

FIG. 9 is a flow chart illustrating generally one example of a technique for performing instrument depth confirmation during an image-guided neurosurgery procedure. At 900, preoperative brain images are obtained using an imaging system, and a target location in the brain is identified. At 902, the images are used to plan an entry point on the subject's skull. At 904, the physical location of the subject's skull is registered (i.e., correlated) to the preoperative brain images. At 906, the planned entry point is located using a frameless surgical navigation alignment wand, or similar techniques, and a burr hole is created at the planned entry point. At 908, the trajectory guiding stereotactic apparatus 100 is mounted in or about the burr hole. At 910, the orientation of the trajectory is adjusted, as desired (e.g., by using the rotate and tilt degrees of freedom of trajectory guide 104, as discussed above), and then fixed. At 912, the instrument 108 is introduced along the trajectory 106. At 914, the positioning apparatus 110 is then coupled to the trajectory guide 104 in a first orientation. At 916, the positions of the reticles 112A-B are adjusted to correspond to the desired target depth (e.g., by using the scales on the slots 116A-B on the respective side arms 128A-B). At 918, the reticles 112A-B are aligned to each other on a display of an intraoperative imaging system (which may be different from the imaging system used to obtain the preoperative images). At 920, a first error (if any) is read along a first sightline 114 between the centers of the aligned reticles 112A-B. At 922, the positioning apparatus 110 is re-oriented with respect to the trajectory guide 104 in a second orientation that is different from the first orientation. At 924, the reticles 112A-B are aligned to each other on the imaging system display. At 926, a second error (if any) is read along a second sightline 114 between the centers of the aligned reticles 112A-B. At 928, the instrument 108 is repositioned using the measurements of the first and second errors; this may include readjusting the trajectory provided by stereotactic apparatus 100, or may simply involve further inserting (or backing off) the instrument 108.

Figure 10:
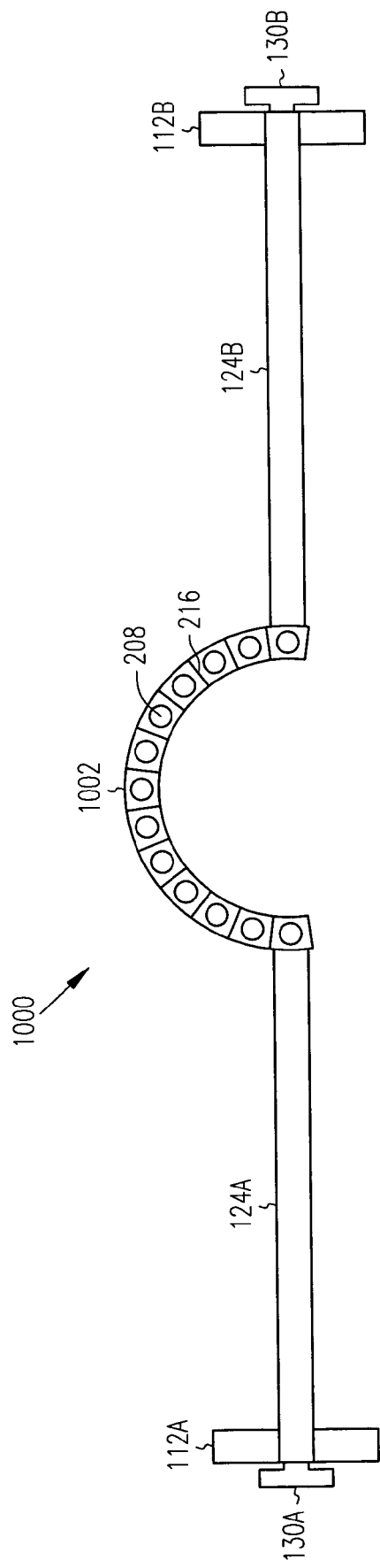
FIG. 10 is a top view schematic diagram illustrating generally an alternative example of a positioning assembly that includes a semicircular or C-shaped indexing ring.

FIG. 10 is a top view of an alternative example of a positioning assembly 1000 that includes a semicircular or C-shaped indexing ring 1002 for seating upon, circularly adjusting with respect to, and securing to the trajectory guide assembly 104. This is advantageous, for example, in an embodiment in which the trajectory guide 104 includes an instrument introducer or other possibly bulky equipment mounted to the stage 200 or inserted into the lumen 202.

Because of the open nature of the C-shaped ring 1002, it may be mounted to (and/or oriented with respect to) the trajectory guide 104 even after such other possibly bulk equipment is already in place. Although the C-shaped indexing ring 1002 may possibly not provide orthogonal first and second sightlines 114 (at least in certain embodiments), even in such embodiments, it still permits a plurality of different orientations for obtaining views along different sightlines 114 for performing separate depth confirmations along such different sightlines 114.

Other Exemplary Trajectory Guides

Although the above examples emphasized verifying whether an instrument has reached a desired target depth along a trajectory 106 using a positioning assembly with imagable locators together with a trajectory guide assembly 104 having separate "rotate" and "tilt" degrees of freedom, the described instrument depth verification devices and techniques apply to a wide variety of other locally-mounted trajectory guides providing an adjustably orientable instrument-guiding trajectory.

Figure 11:
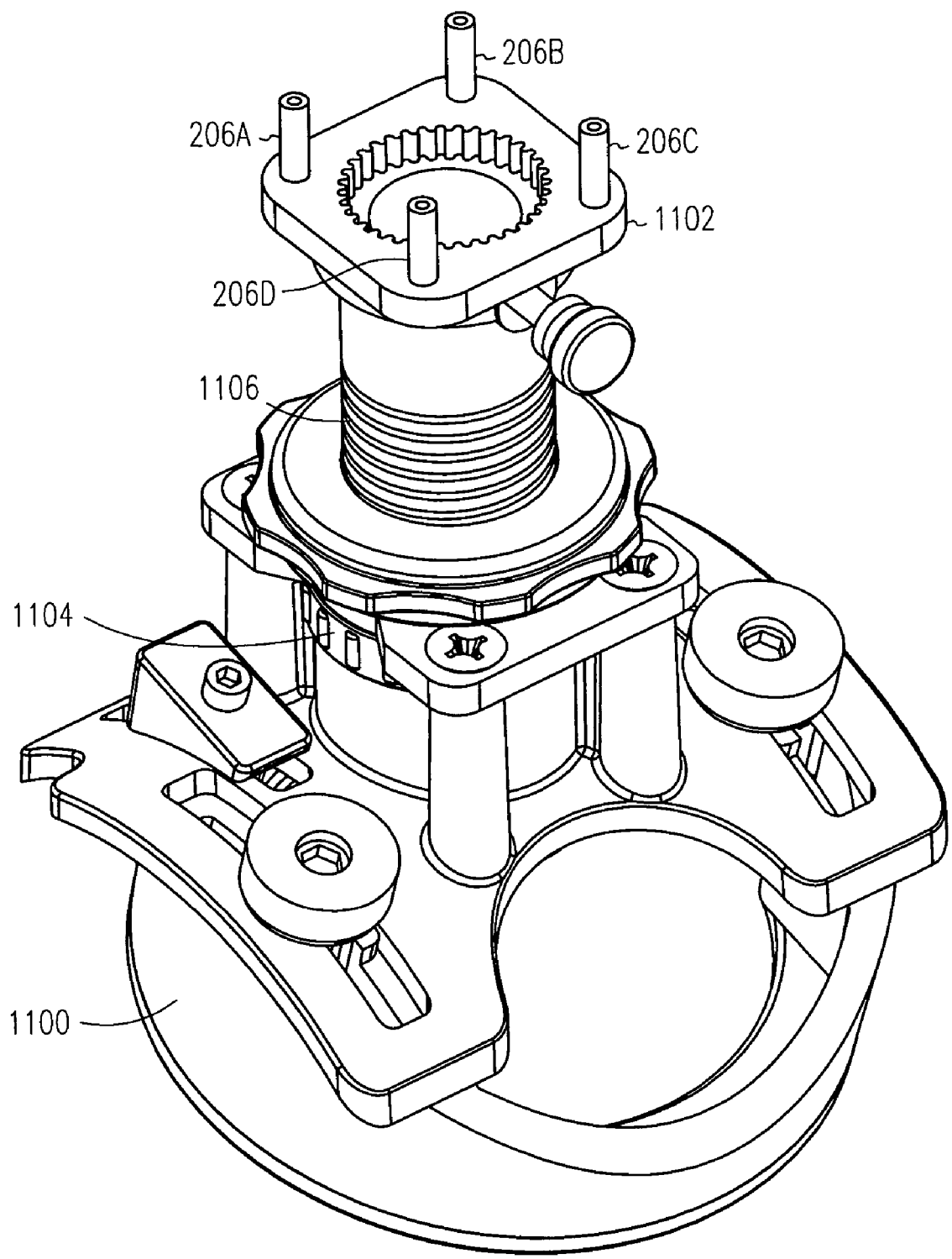
FIG. 11 is a schematic diagram illustrating generally a perspective view of a trajectory guide assembly including an adjustable-height stage.

For example, FIG. 11 is a schematic diagram illustrating generally a perspective view of a trajectory guide assembly 1100 including an adjustable-height stage 1102 for receiving a multilumen or other insert providing one or more instrument guide lumens defining the trajectory 106. The height of the stage 1102 above the burr hole or other entry portal is adjusted by turning a dial 1104 that engages a threaded portion 1106 of a member supporting the stage 1102. One example of aspects of such a trajectory guide assembly 1100 is described in Mazzocchi et al. U.S. patent application Ser. No. 10/370,090, entitled "TRAJECTORY GUIDE WITH ANGLED OR PATTERNED GUIDE LUMENS OR HEIGHT ADJUSTMENT," filed on even date herewith, which is incorporated herein by reference in its entirety, including its description of height adjustment for a locally-mounted adjustably orientable trajectory guide. In FIG. 11, the stage 1102 includes posts 206 or other suitable structures for receiving and seating a rotatable circular or semicircular ring 123 portion of a positioning assembly 110 that includes imagable depth confirmation locators, such as described above.

Moreover, in one such height adjustable trajectory guide embodiment, positioning assembly 110 need not include slots or other adjustable coupling of the side arms 128A-B to the radial arms 124A. Instead, the stage 1102 is first adjusted to a desired height from the target. Then, an appropriate unitary positioning assembly, with side arms 128A-B having lengths fabricated to correspond to a particular depth or the like, is selected from a kit of such pre-fabricated positioning assemblies with varying length side arms 128A-B corresponding to various possible target depths (in one example, the particular depth is printed on the particular assembly, thereby allowing the user to easily select the desired depth). The target depth confirmation is then performed using the particularly selected positioning assembly that corresponds to the desired target depth.

Figure 12:
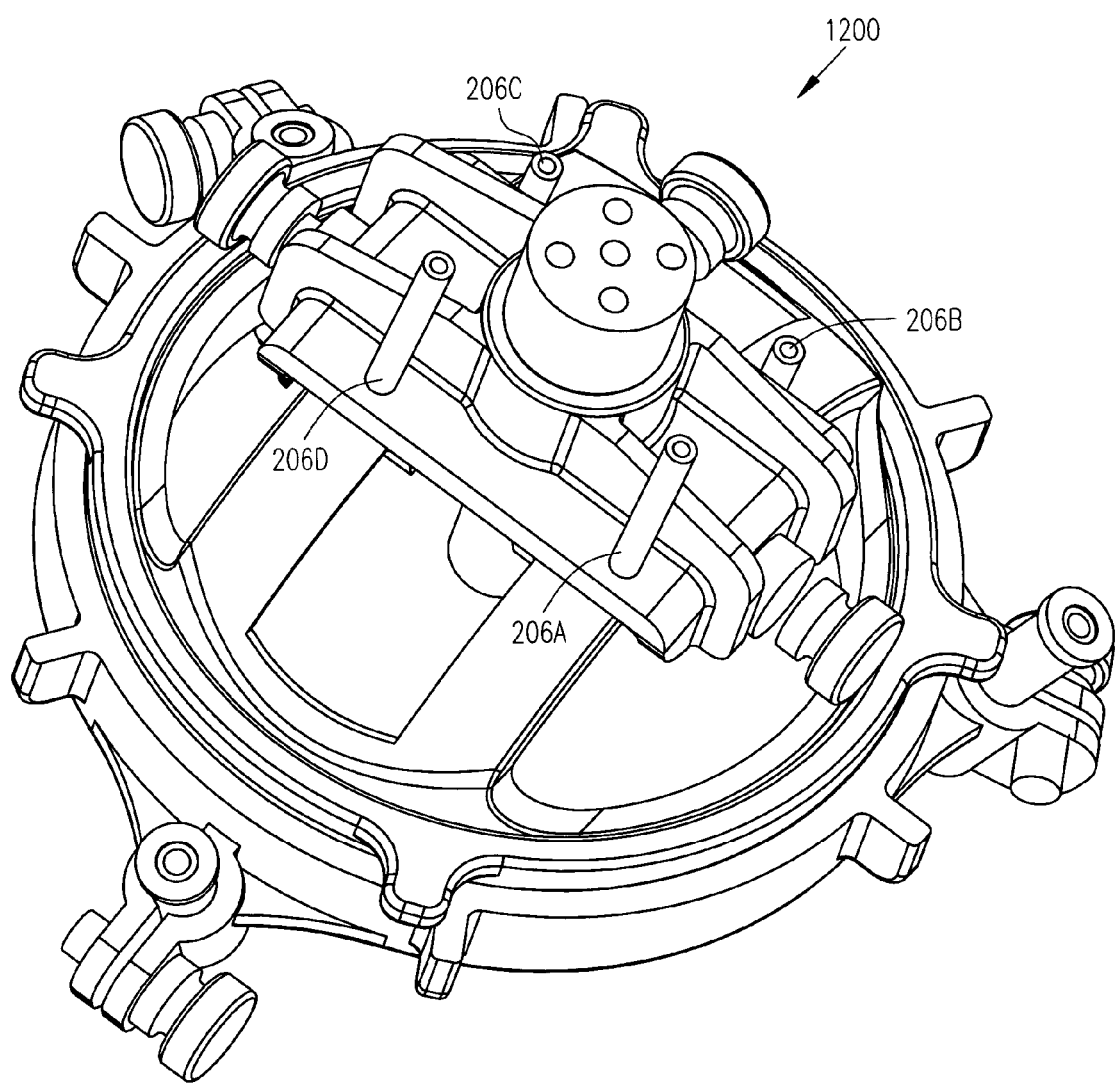
FIG. 12 is a schematic diagram illustrating generally an alternative trajectory guide assembly including an apparatus for receiving and seating a positioning assembly bearing imagable depth confirmation locators.

FIG. 12 is a schematic diagram illustrating generally, by way of example, but not by way of limitation, one embodiment of an alternative trajectory guide assembly 1200 carrying an instrument guide insert 1202 having at least one guide lumen, and including posts 206 or other suitable structures for receiving and seating a rotatable circular or semicircular ring 123 portion of a positioning assembly 110 that includes imagable depth confirmation locators, such as described above. Certain portions of the trajectory guide assembly 1200 are described in Matthew Solar's U.S. patent application Ser. No. 10/325,615, entitled ORGAN ACCESS DEVICE AND METHOD filed on Dec. 20, 2002, commonly assigned to Image-Guided Neurologics, Inc., which is incorporated herein by reference in its entirety, including its description of portions of a trajectory guide assembly as illustrated in FIG. 12 of the present document.

Figure 13:
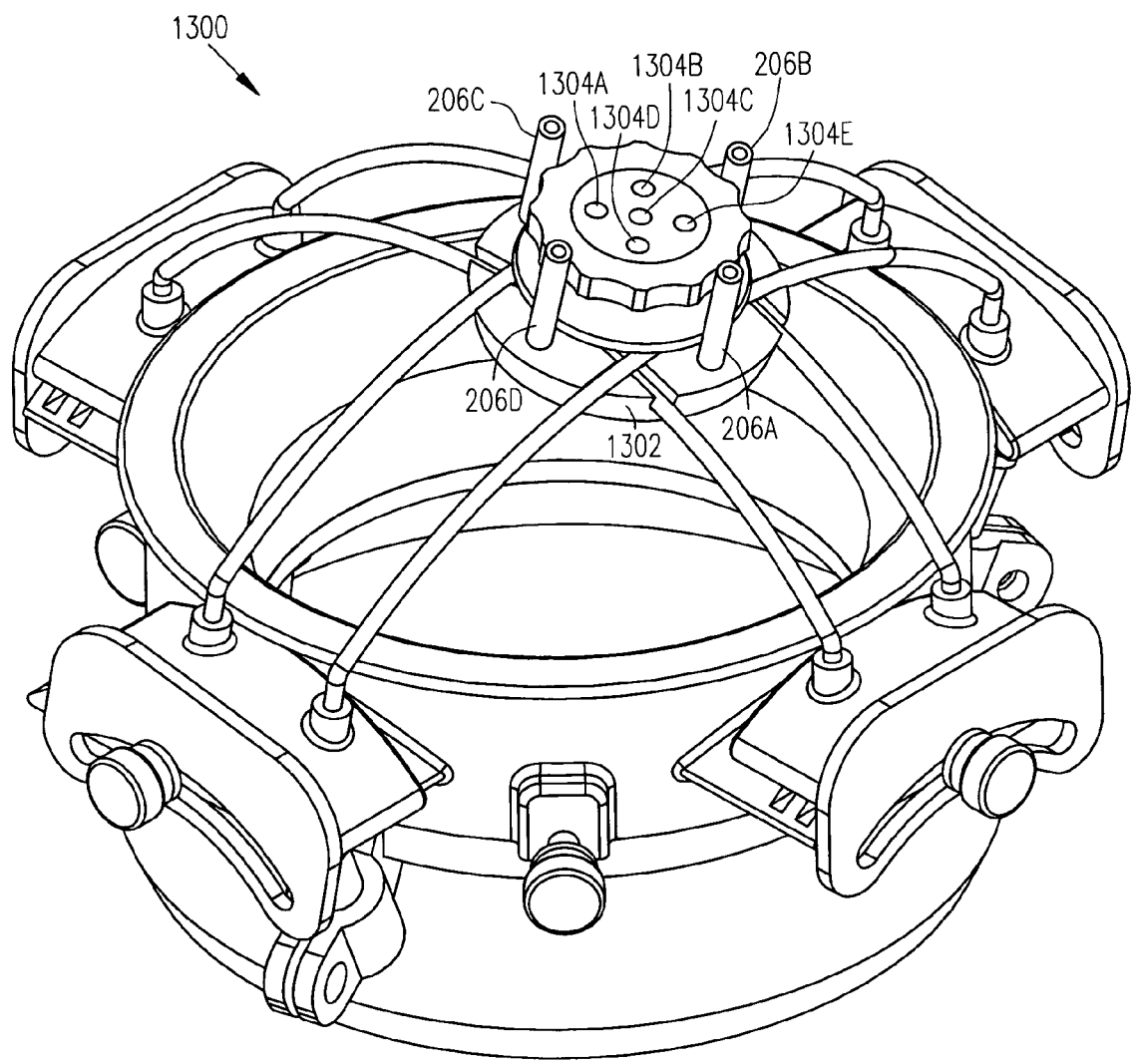
FIG. 13 is a schematic diagram illustrating generally another alternative trajectory guide assembly including an apparatus for receiving and seating a positioning assembly that includes imagable depth confirmation locators.

FIG. 13 is a schematic diagram illustrating generally, by way of example, but not by way of limitation, another embodiment of an alternative trajectory guide assembly 1300 carrying an instrument guide 1302 that includes at least one guide lumen 1304 and posts 206 or other suitable structures for receiving and seating a rotatable circular or semicircular ring 123 portion of a positioning assembly 110 that includes imagable depth confirmation locators, such as described above. Certain portions of trajectory guide assembly 1300 are described in Matthew Solar's U.S. patent application Ser. No. 10/325,615, entitled ORGAN ACCESS DEVICE AND METHOD, filed on Dec. 20, 2002, commonly assigned to Image-Guided Neurologics, Inc., which is incorporated herein by reference in its entirety, including its description relevant to a trajectory guide assembly as illustrated in FIG. 13 of the present document.

Figure 14:
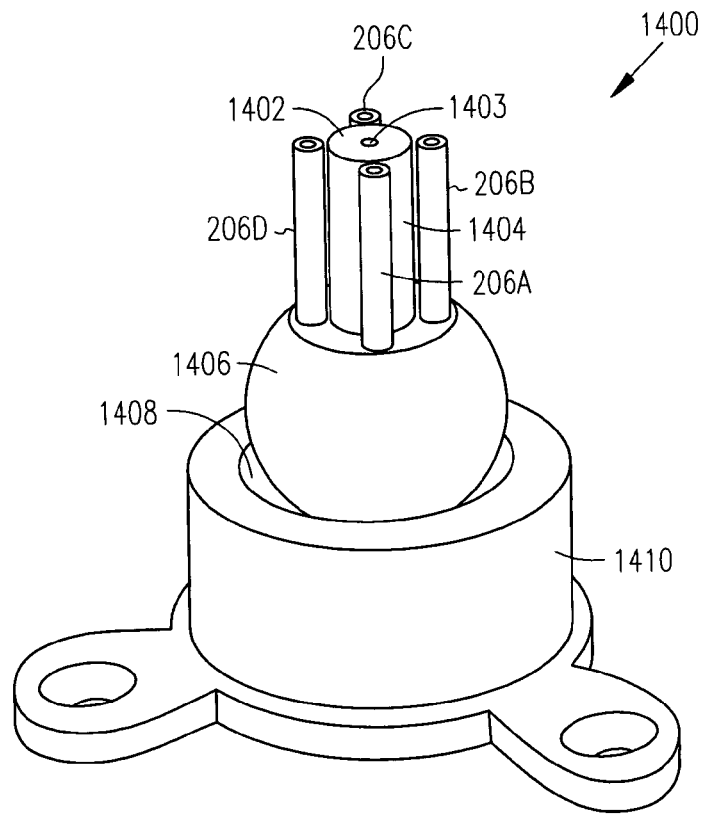
FIG. 14 is a schematic diagram illustrating generally a first ball-and-socket type trajectory guide assembly that includes an apparatus for receiving and seating a positioning assembly that includes imagable depth confirmation locators.

FIG. 14 is a schematic diagram illustrating generally, by way of example, but not by way of limitation, another embodiment of an alternative trajectory guide assembly 1400 carrying an instrument guide 1402 having at least one guide lumen 1403, and having a barrel sleeve portion 1404 that extends into a ball 1406 that is received within a socket 1408 portion of a mounting base 1410. The trajectory guide assembly 1400 also includes posts 206 or other suitable structures for receiving and seating a rotatable circular or semicircular ring 123 portion of a positioning assembly 110 that includes imagable depth confirmation locators, such as described above. In this example, the ball 1406 is positioned just above a burr hole entry portal. Certain portions of trajectory guide assembly 1400 are described Truwit U.S. Pat. No. 6,267,769, which is incorporated herein by reference in its entirety, including its description relevant to a trajectory guide assembly and mounting base as illustrated in FIG. 14 of the present document.

Figure 15:
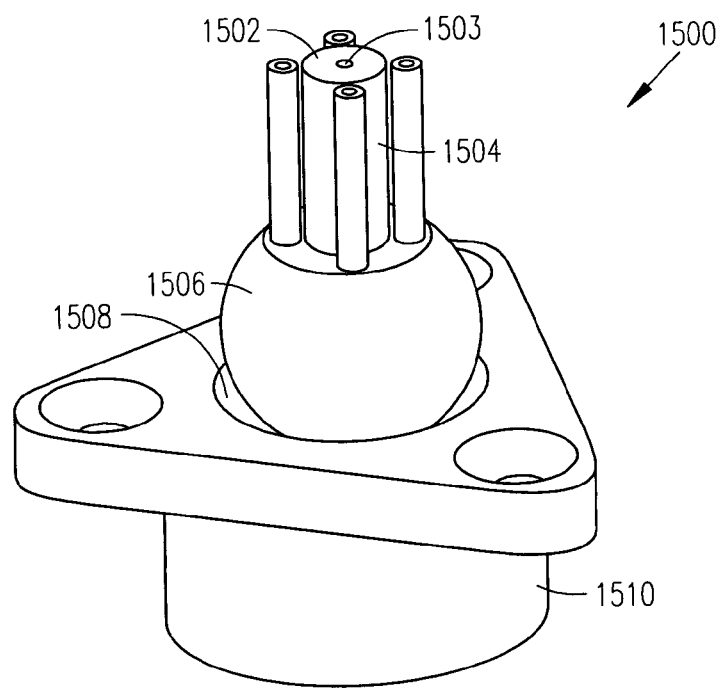
FIG. 15 is a schematic diagram illustrating generally a second ball-and-socket type trajectory guide assembly that includes an apparatus for receiving and seating a positioning assembly that includes imagable depth confirmation locators.

FIG. 15 is a schematic diagram illustrating generally, by way of example, but not by way of limitation, another embodiment of an alternative trajectory guide assembly 1500 carrying an instrument guide 1502 having at least one guide lumen 1503, and having a barrel sleeve portion 1504 that extends into a ball 1506 that is received within a socket 1508 portion of a mounting base 1510. The trajectory guide assembly 1500 also includes posts 206 or other suitable structures for receiving and seating a rotatable circular or semicircular ring 123 portion of a positioning assembly 110 that includes imagable depth confirmation locators, such as described above. In this example, the ball 1506 is positioned at least partially within the burr hole entry portal. Certain portions of trajectory guide assembly 1500 are described Truwit U.S. Pat. No. 5,993,463, which is incorporated herein by reference in its entirety, including its description relevant to a trajectory guide assembly and mounting base as illustrated in FIG. 15 of the present document.

Figure 16:
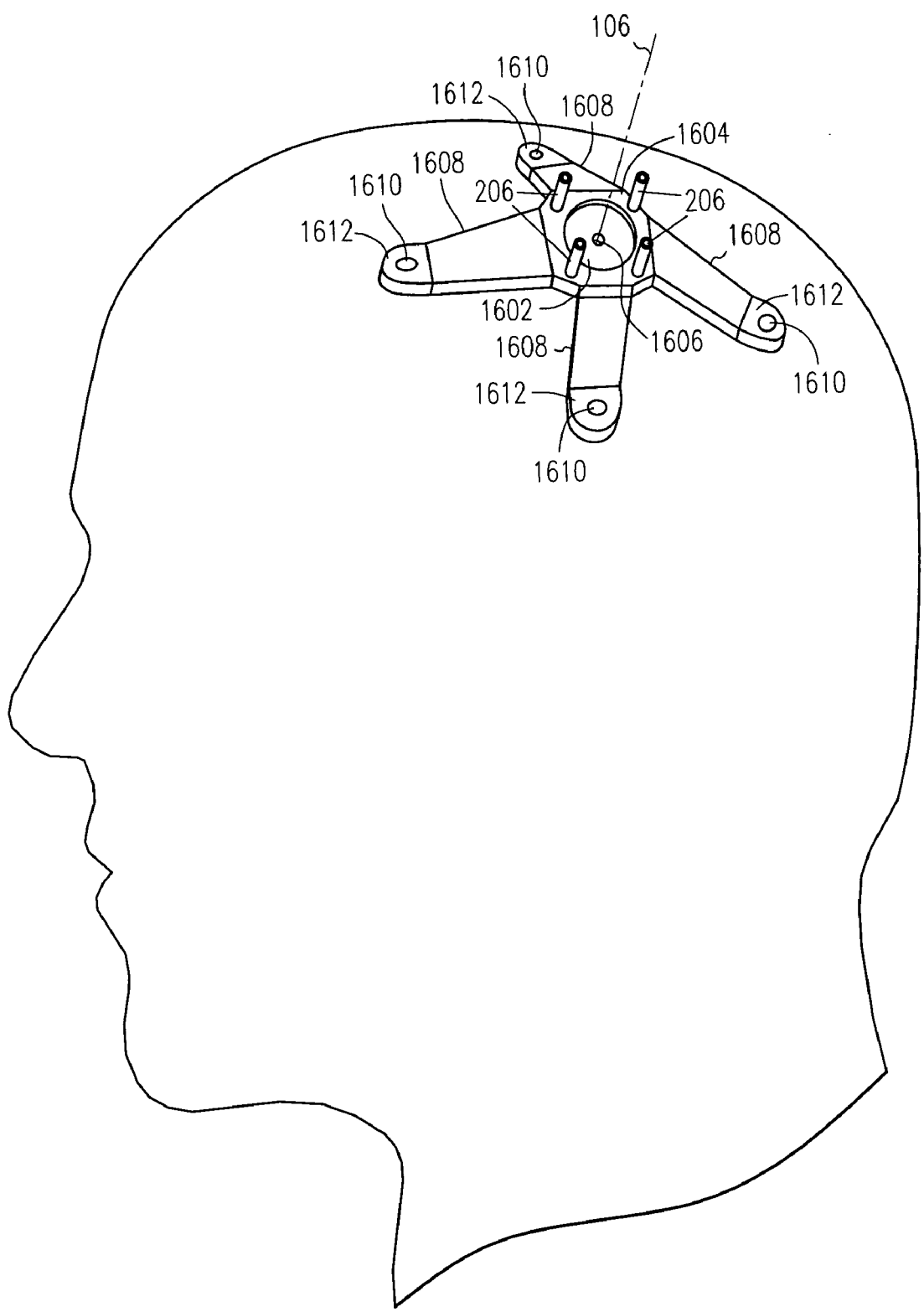
FIG. 16 is a schematic diagram illustrating generally an example of a custom-formed trajectory guide that includes an apparatus for receiving and seating a positioning assembly that includes imagable depth confirmation locators.

FIG. 16 is an example of a trajectory guide 1600 that is custom-formed (e.g., using known rapid prototyping and tooling techniques and preoperative images of a desired target in a subject) such that an instrument guide 1602 portion of a working platform 1604 includes at least one guide lumen 1606 providing a concentric trajectory 106 directed through the center of a burr hole or other entry portal to intersect a portion of the desired target within the subject. In one example, the platform 1604 is oriented as desired by custom manufacturing (e.g., tailored to a particular procedure on a particular subject) the size or shape of legs 1608, which are mounted to the subject's skull, such as by using bone screws extending through holes 1610 through respective feet 1612 extending outwardly from respective legs 1608. In this example, the working platform 1604 includes posts 206 or other suitable structures for receiving and seating a rotatable circular or semicircular ring 123 portion of a positioning assembly 110 that includes imagable depth confirmation locators, such as described above.

CONCLUSION

The techniques discussed herein may also be useful for accessing locations within any material, particularly where access to the material is limited by a finite-sized entry portal. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An apparatus comprising:
   a mounting base, configured to be locally secured relative to an entry portal in a surface;
   a trajectory guide assembly, adjustably coupled to the mounting base, the trajectory guide assembly including at least one adjustably orientable instrument guide structure to establish a trajectory for an instrument to be introduced through the entry portal in the surface;
   first and second imagable locators, coupled to the trajectory guide assembly at respective different first and second positions that are located away from the trajectory, the first and second imagable locators defining a first line therebetween that intersects the trajectory; and
   wherein the first and second imagable locators are each adjustably coupled to the trajectory guide assembly such that each of the first and second imagable locators are moveable to adjust the first line to substantially orthogonally intersect the trajectory at different points along the trajectory.

2. The apparatus of claim 1, in which the first line continues to intersect the trajectory as the trajectory guide assembly is adjusted with respect to the mounting base to orient the instrument guide structure.

3. The apparatus of claim 1, in which the first and second imagable locators are positioned away from the trajectory guide assembly such that, when the mounting base is affixed to a skull-shaped surface and the trajectory guide assembly is coupled to the mounting base, the first and second imagable locators are located on opposite sides of the skull-shaped surface.

4. The apparatus of claim 1, in which the first and second imagable locators are carried by at least one positioning assembly that is couplable to the trajectory guide assembly in different orientations to permit the first line to intersect the trajectory from different directions.

5. The apparatus of claim 4, in which the at least one positioning assembly includes at least one positioner configured to permit axial adjustment of locations of at least one of the first and second imagable locators to adjust the first line to intersect the trajectory at different points along the trajectory.

6. The apparatus of claim 1, in which the first and second imagable locators include alignment reticles, the alignment reticles comprising a pattern of concentric circles spaced about a centerpoint of the first and second imagable locators, and crosshairs that intersect at the respective centerpoints of the first and second imagable locators to enable a user to sight along the first line.

7. An apparatus for use with a trajectory guide assembly that is adjustably coupled to a mounting base that is configured to be locally secured relative to an entry portal in a surface, the trajectory guide assembly defining a trajectory, through the entry portal, along which an instrument is introduced, the apparatus configured for confirming, using an imaging system, a depth to which the instrument is inserted along the trajectory, the apparatus comprising:
   a positioning assembly that is adapted to be coupled to the trajectory guide assembly and including a first and second side arm coupled to the positioning assembly at respective different first and second locations away from the trajectory, the first and second side arms each extending and axially adjustable along a longitudinal axis;
   first and second imagable locators, each coupled to a respective one of the first and second side arms of the positioning assembly such that, when the positioning assembly is coupled to the trajectory guide assembly, a first line between the first and second locators intersects the trajectory; and
   wherein the positioning assembly includes at least one positioner configured to permit adjustment of locations of the first and second imagable locators to adjust the first line to intersect the trajectory at different points along the trajectory.

8. The apparatus of claim 7, in which the first line substantially orthogonally intersects the trajectory.

9. The apparatus of claim 7, in which the positioning assembly is adapted to be adjustably coupled to the trajectory guide to adjust the first line to intersect the trajectory at different points along the trajectory.

10. The apparatus of claim 7, in which the first line continues to orthogonally intersect the trajectory as the trajectory guide assembly is adjusted with respect to the mounting base.

11. The apparatus of claim 7, in which the first and second imagable locators are positioned away from the trajectory guide assembly such that, when the mounting base is affixed to a skull-shaped surface and the trajectory guide assembly is coupled to the mounting base and the positioning assembly is coupled to the trajectory guide assembly, the first and second imagable locators are located on opposite sides of the skull-shaped surface.

12. The apparatus of claim 7, in which the positioning assembly is couplable to the trajectory guide assembly in different orientations to permit the first line to intersect the trajectory from different directions.

13. The apparatus of claim 7, in which the first and second imagable locators include alignment reticles.

14. An apparatus comprising:
   a mounting base, configured to be locally secured relative to an entry portal in a surface of a skull;
   a trajectory guide assembly, adjustably coupled to the mounting base, the trajectory guide assembly including:

an instrument guide structure that is configured to establish a trajectory for an instrument to be introduced through the entry portal in the surface;

a rotational joint, that permits the instrument guide structure to rotate about a first axis concentric to the entry portal and orthogonal to the surface; and an arc-shaped joint, that permits the instrument guide to tilt to adjust an angle between the trajectory and the first axis concentric to the entry portal; and a positioning assembly that includes first and second radial arms that are operable to be coupled to the instrument guide structure, first and second side arms that are adjustably coupled to a respective one of the first and second radial arms, and first and second imagable locators coupled to respective distal ends of the first and second side arms, the first and second side arms extending generally parallel to each other and orthogonal to the first and second radial arms, such that a first line formed between the first and second side arms intersects the trajectory, with the first and second imagable locator operable to indicate whether the instrument has reached a target along the trajectory.

15. The apparatus of claim 14, in which the first and second imagable locators include first and second reticles such that they are positioned on opposing side of the skull, the first and second imagable reticles including respective first and second centers, with the first line formed between the centers of the first and second imagable reticles, and the first line intersects the trajectory statically and while the instrument guide is being positioned using the rotational and arc-shaped joints.

16. The apparatus of claim 15, in which the positioning assembly is rotatably coupled to the instrument guide structure to permit at least some rotation of the first and second reticles about the skull such that the first line intersects the trajectory in a plurality of different directions.

17. The apparatus of claim 15, in which the positioning assembly includes at least one positioner configured to permit adjustment of locations of the first and second reticles to adjust the first line to intersect the trajectory at different points along the trajectory.

18. The apparatus of claim 15, in which the first and second reticles are adjustably coupled to the positioning assembly to permit the first and second reticles to be moved toward or away from the skull.

19. A method comprising:
locally mounting a base relative to an entry portal in a surface;
obtaining a desired trajectory through the entry portal toward a target beyond the surface;
inserting an instrument along the trajectory;
positioning first and second imagable locators on opposing sides of the trajectory; and
determining a depth of the instrument along the trajectory to ensure that the instrument has reached the target, in which the determining includes aligning the first and second imagable locators with the instrument and obtaining an image of the first and second imagable locators aligned with the instrument to determine the depth of the instrument using the first and second imagable locators.

20. The method of claim 19, in which the locally mounting the base includes securing a trajectory guide in or about a burr hole.

21. The method of claim 19, in which the obtaining the desired trajectory includes adjusting an instrument guide with respect to the base.

22. The method of claim 21, in which the obtaining the desired trajectory includes custom-fabricating an instrument guide, to point the trajectory toward the target, using images of the target.

23. The method of claim 19, in which the obtaining the desired trajectory includes at least one of:
rotating an instrument guide about an axis concentric to the burr hole and orthogonal to the surface; and
tilting the instrument guide to adjust an angle between the trajectory and the axis.

24. The method of claim 19, in which the positioning the first and second imagable locators includes coupling a positioning assembly to an instrument guide in one of a plurality of possible orientations in which a first line between the first and second imagable locators orthogonally intersects the trajectory.

25. The method of claim 19, in which the positioning the first and second imagable locators includes coupling at least a portion of a positioning assembly to an instrument guide in one of a plurality of possible positions such that a first line between the first and second imagable locators intersects the trajectory in a desired one of a plurality of different points along the trajectory, the desired one of the plurality of different points along the trajectory corresponding to a location of the target on the trajectory.

26. A method comprising:
locally mounting a base relative to an entry portal in a surface;
adjusting an orientation of an instrument guide structure, with respect to the base, to obtain a desired trajectory through the entry portal toward a target beyond the surface;
inserting an instrument along the trajectory using the instrument guide structure to guide the instrument along the trajectory;
coupling first and second imagable locators to the instrument guide structure such that a first line between the first and second imagable locators orthogonally intersects the trajectory; and
determining a depth of the instrument along the trajectory to ensure that the instrument has reached the target, in which the determining includes obtaining an image of the first and second imagable locators and the instrument.

27. The method of claim 26, in which the locally mounting the base includes securing a trajectory guide in or around a burr hole.

28. The method of claim 26, in which the adjusting the orientation of the instrument guide structure includes at least one of:
rotating a portion of the instrument guide structure about an axis concentric to the burr hole and orthogonal to the surface; and
tilting a portion of the instrument guide structure to adjust an angle between the trajectory and the axis.

29. The method of claim 26, in which the positioning the first and second imagable locators includes coupling a positioning assembly to the instrument guide in one of a plurality of possible orientations in which a first line between the first and second imagable locators intersects the trajectory.

30. The method of claim 26, in which the positioning the first and second imagable locators includes coupling at least a portion of a positioning assembly to the instrument guide in one of a plurality of possible positions such that a first line between the first and second imagable locators intersects the trajectory in a desired one of a plurality of different points along the trajectory, the desired one of the plurality of different points along the trajectory corresponding to a location of the target on the trajectory.

31. The method of claim 26, in which the positioning the first and second imagable locators includes moving at least one of the imagable locators toward or away from the trajectory to obtain a desired position, and securing the at least one of the imagable locators at the desired position.

* * * * *